US010213222B2

(12) United States Patent
Guo et al.

(10) Patent No.: US 10,213,222 B2
(45) Date of Patent: Feb. 26, 2019

(54) METHODS FOR THREAD TRANSECTION OF A SOFT TISSUE

(71) Applicants: Joseph Guo, Monterey Park, CA (US); Danzhu Guo, Green Bay, WI (US); Danqing Guo, De Pere, WI (US)

(72) Inventors: Joseph Guo, Monterey Park, CA (US); Danzhu Guo, Green Bay, WI (US); Danqing Guo, De Pere, WI (US)

( * ) Notice: Subject to any disclaimer, the term of this patent is extended or adjusted under 35 U.S.C. 154(b) by 270 days.

(21) Appl. No.: 15/270,907

(22) Filed: Sep. 20, 2016

(65) Prior Publication Data

US 2017/0035451 A1    Feb. 9, 2017

Related U.S. Application Data

(63) Continuation-in-part of application No. 13/870,291, filed on Apr. 25, 2013, which is a continuation-in-part of application No. 13/460,246, filed on Apr. 30, 2012, now Pat. No. 9,381,033.

(51) Int. Cl.
| | | |
|---|---|---|
| *A61B 17/32* | (2006.01) | |
| *A61B 17/3205* | (2006.01) | |
| *A61B 17/34* | (2006.01) | |
| *A61B 17/14* | (2006.01) | |
| *A61B 17/3207* | (2006.01) | |

(52) U.S. Cl.
CPC .... *A61B 17/320036* (2013.01); *A61B 17/149* (2016.11); *A61B 17/3205* (2013.01); *A61B 17/32053* (2013.01); *A61B 17/34* (2013.01); *A61B 17/3403* (2013.01); *A61B 2017/32006* (2013.01); *A61B 2017/320733* (2013.01)

(58) Field of Classification Search
CPC ............ A61B 17/32; A61B 17/32002; A61B 17/3205; A61B 17/32053; A61B 17/3209; A61B 17/320036; A61B 17/32093; A61B 17/34; A61B 17/3403; A61B 2017/320028; A61B 2017/32006; A61B 2017/320733
USPC .................................. 606/167, 170
See application file for complete search history.

(56) References Cited

U.S. PATENT DOCUMENTS 6,915,796 B2    7/2005  Sung
9,314,260 B2 *  4/2016  Porshinsky ...... A61B 17/32003

OTHER PUBLICATIONS

Office Action, 6 pages, dated Sep. 20, 2018, from counterpart Mexico application No. MX/a/2014/013195 filed Oct. 30, 2014.

* cited by examiner

*Primary Examiner* — Melanie R Tyson
(74) *Attorney, Agent, or Firm* — Fulwider Patton LLP

(57) ABSTRACT

A method and apparatus for transecting soft tissue, such as a ligament, and more particularly, the transverse carpal ligament. A pair of hollow introducer needles can be used to rout a thread-like, smooth and non-abrasive cutting element around tissue, such as a soft tissue, to enable a transection of the soft tissue using minimally invasive techniques. The cutting element is routed into position about the target soft tissue such that the cutting element both enters and exits the body from the same side of the soft tissue. The smooth and non-abrasive exterior surface of the cutting element serves to provide a kerf-less cut.

12 Claims, 19 Drawing Sheets

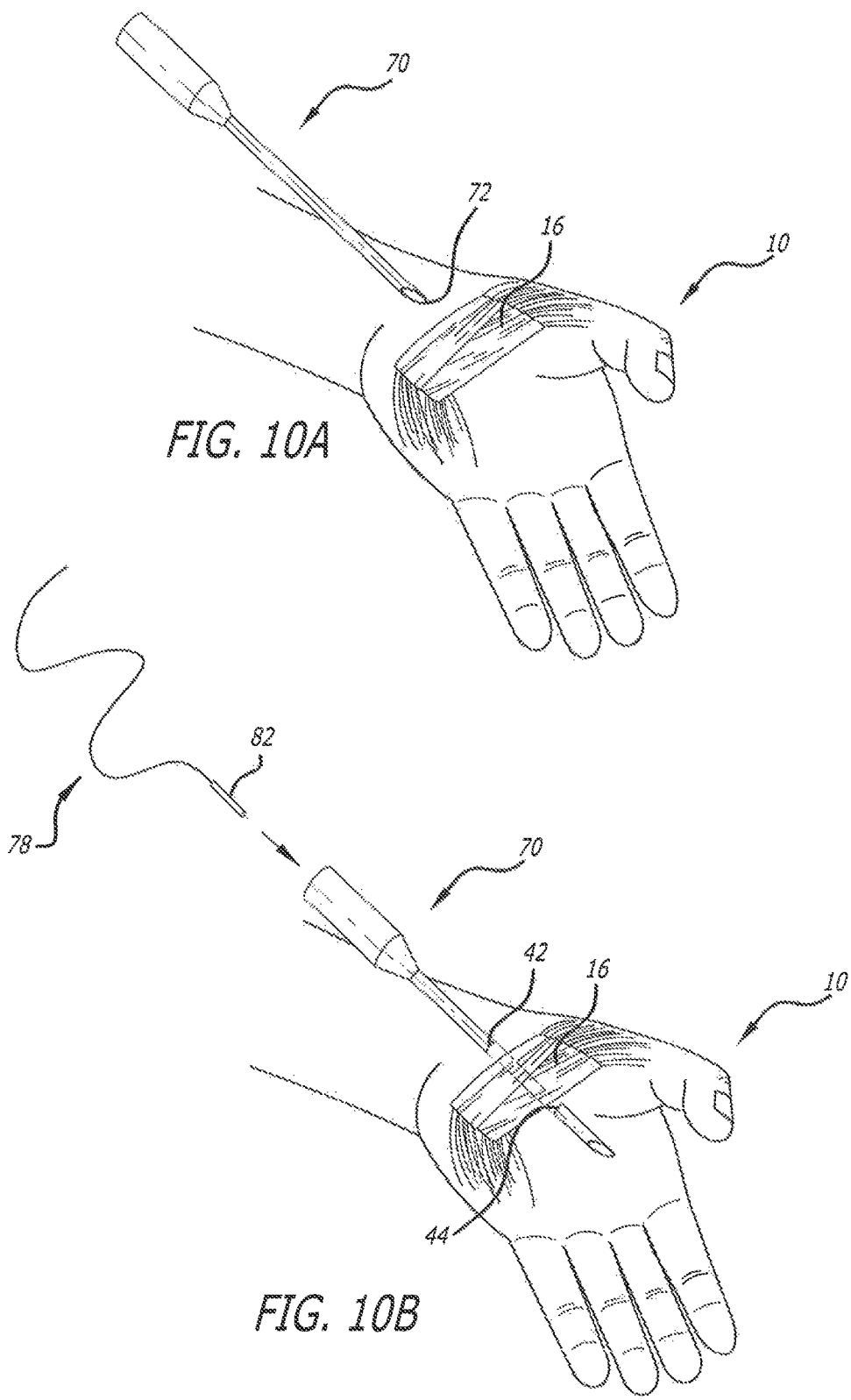

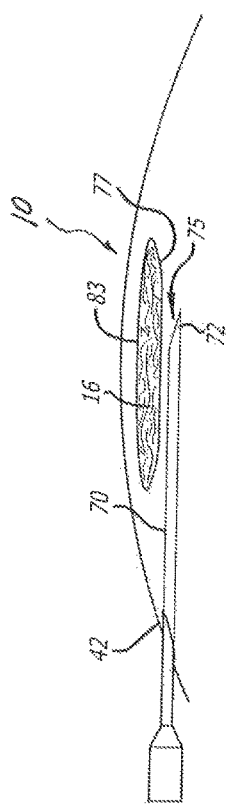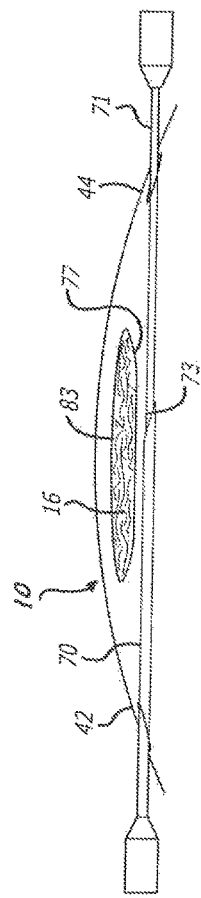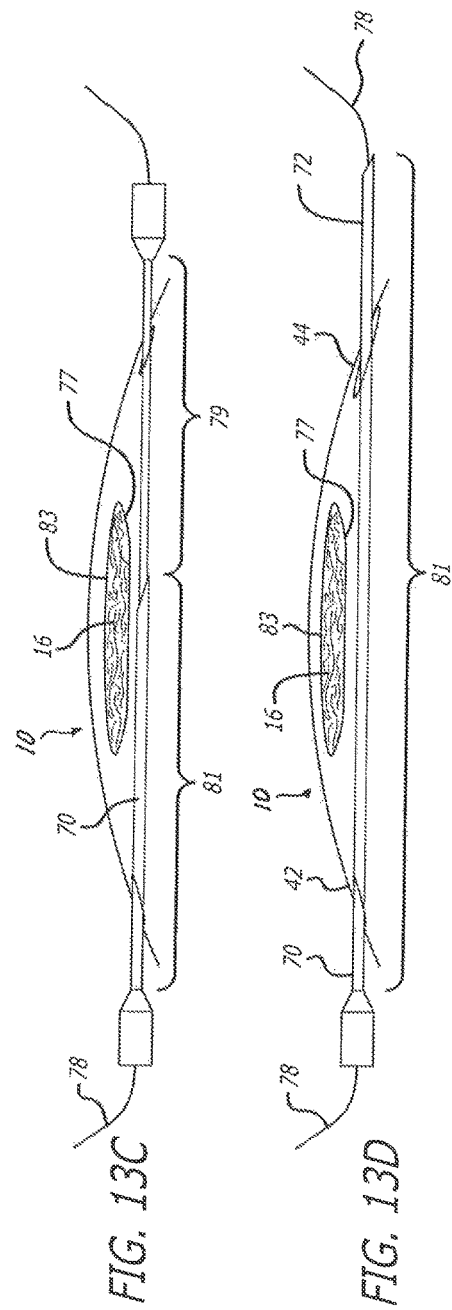
FIG. 13A
FIG. 13B
FIG. 13C
FIG. 13D

METHODS FOR THREAD TRANSECTION OF A SOFT TISSUE

CROSS-REFERENCES TO RELATED APPLICATIONS

This application is a continuation-in-part of U.S. Ser. No. 13/870,291, filed on Apr. 25, 2013, incorporated by reference herein in its entirety, which is a continuation-in-part of U.S. Ser. No. 13/460,246, filed on Apr. 30, 2012, incorporated by reference herein in its entirety.

The present invention is generally directed to surgical methods for the transection, by minimally invasive means, of soft tissue such as, for example, the transverse carpal ligament that is commonly released as a treatment for carpal tunnel syndrome.

BACKGROUND

Many people suffer from injury to the soft tissues of the wrist and carpal tunnel, often caused by frequent, sustained repetitive motion involving the hands. Repetitive activities which require the same or similar hand/wrist action can result in injuries which have been collectively referred to as Cumulative Repetitive Stress Syndrome or Repetitive Strain Injury. The most familiar and common of such wrist injuries is known as carpal tunnel syndrome which produces pain, discomfort, nerve conduction disturbances, and impairment of function of the hand and sometimes the arm as well. The most common symptoms of this condition include intermittent pain and numbness of the hand.

Carpal tunnel syndrome occurs when the median nerve which runs from the forearm into the hand, becomes pressed or squeezed at the wrist. The median nerve provides feeling in one's thumb and along with index, middle and ring ringers. The median nerve controls sensations to the palmar side of the thumb and these fingers as well as impulses to some muscles in the hand which allow the fingers and thumb to move. The median nerve receives blood, oxygen and nutrients through a microvascular system which is present in the connective tissue surrounding the nerve fiber. Increased pressure on the nerve fiber can constrict these microvessels and will reduce the blood flow to the median nerve. Any prolonged deprivation of oxygen and nutrients can result in severe nerve damage.

The median nerve passes through the carpal tunnel, a canal in the wrist surrounded by the carpal bones on three sides and a fibrous sheath called the transverse carpal ligament on the fourth side. In addition to the median nerve, the nine flexor tendons in the hand pass through this canal. When compressed, the median nerve will cause pain, weakness or numbness in the hand and wrist which may also radiate up along the arm. The median nerve can be compressed by a decrease in the size of the carpal canal itself or an increase in the size of its contents (i.e. such as the swelling of the flexor tendons and of the lubrication tissue surrounding these flexor tendons), or both. For example, conditions that irritate or inflame the tendons can cause them to swell. The thickening of irritated tendons or swelling of other tissue within the canal narrows the carpal canal, causing the median nerve to be compressed. The cross-sectional area of the tunnel also changes when the hand and wrist changes positions. Wrist flexion or extension can decrease the cross-sectional area, thus increasing the pressure exerted on the median nerve. Flexion also causes the flexor tendons to somewhat rearrange which can also compress the median nerve. For example, simple bending of the wrist at a 90 degree angle will decrease the size of the carpal canal. Without treatment, carpal tunnel syndrome can lead to chronic neural muscular disorders of the hand and sometimes the arm.

Treatment for carpal tunnel syndrome includes a variety of non-surgical as well as surgical procedures, wherein carpal tunnel release is one of the most common surgical procedures that is performed. Such surgery involves the severing of the transverse carpal ligament to relieve the pressure on the median nerve and is commonly performed via either open or endoscopic methods. In open methods, the skin lying over the carpal tunnel is incised after which the transverse carpal ligament is transected under direct vision. The skin is then reapproximated with sutures. Endoscopic methods require incision of the skin in one or more locations to allow for the insertion of an endoscope along with various tools that are needed to transect the ligament. Such tools typically include a combination of a specially configured scalpel and guide instrument. The insertion of such tools into proper position below, above or both below and above the target ligament further requires the formation of one or more pathways in the hand with attendant trauma to the surrounding tissue and the potential for nerve damage as well as a more protracted post-surgical healing process. Additionally, the use of a scalpel typically requires multiple passes thereof in order to complete a transection which causes a complex pattern of cuts to be imparted onto the severed ligament surfaces.

Less invasive techniques have been proposed including for example the use of flexible saw elements that are introduced into the hand and positioned adjacent to or wrapped about a portion of the target ligament after which the saw element is reciprocated to cut the tissue. A substantial disadvantage of a cut that is made by a saw-like instrument as opposed to a knife-like instrument is inherent in the fact that a kerf is created. The material that is removed from the kerf is either deposited in and around the surgical site or additional steps must be taken to retrieve such material. Additionally, the cut surfaces that are created by a saw tend to be relatively rough and abraded with microtrauma on the cutting surface that may increase inflammatory response (edema, erythema, heat and pain), could result in local tissue adhesions and scarring which can delay or complicate the healing process.

Alternatively, techniques have been proposed wherein a taut wire, string or filament is used to cut a ligament. The cut is achieved either by the tautening of the cutting element or alternatively, by reciprocating the taut element. Disadvantages associated with such an approach are inherent in the less than optimal geometry by which a taut wire can be brought to bear on the target ligament and by the invasiveness of the tightening apparatus.

A new method and apparatus is needed with which tissue such as a ligament can be percutaneously accessed and transected so as to cause a very minimal amount of disruption to the surrounding tissue and by which a smooth, kerf-less cut is achieved.

SUMMARY OF THE INVENTION

The present invention provides for the minimally-invasive transection of tissue such as a ligament. The method and apparatus obviate the need for any incisions, minimizes disruption of the tissue surrounding the target ligament, enables a smooth kerf-less cut of the target ligament to be achieved, requires no suturing and can be easily and quickly performed in a clinic setting.

More particularly, the invention provides for the introduction of a thin and flexible thread-like cutting element, which is smooth and non-abrasive, into the body and its routing about the target ligament. Subsequent manipulation of the protruding ends of the smooth cutting element serves to transect the ligament by a smooth kerf-less cut. Particular methods and apparatus for routing the cutting element are disclosed in co-pending U.S. Ser. No. 13/870,291, filed on Apr. 25, 2013. In this co-pending application, FIGS. 10A-J and the paragraphs relaed thereto disclose a method in which a hollow introducer needle serves as a router tool and is inserted into a first location of the patient proximal to the tissue to be transected. The introducer needle is then advanced past one side of the target tissue (for example, a ligament) and allowed to exit a second location on the patient adjacent to the target tissue. The cutting element is inserted into the needle's proximal end while the needle is in the position described above. The cutting element is extended through the length of the needle and approximately one half of the cutting element is pulled from the distal end of the needle. The needle is then proximally retracted from the hand to leave the cutting element in place in the hand such that a sizable portion thereof protrudes from the first location as well as from the second location. The hollow needle is then reinserted into the first location and adjacent to the proximally protruding length of cutting element, is extended through the hand on a second side (immediately above) of the ligament and out of the second location. The distally protruding portion of the cutting element is then fed into the distal end of the hollow needle in place within the hand and extended through its length so as to emerge from the proximal end of the needle after which the needle is retracted from the hand. The routing of the cutting element about the ligament is thereby complete leaving the cutting element in position for the transection. Alternatively, one end of the cutting element may be initially introduced into the distal end of the needle and extended there through. After retraction of the needle and reinsertion into and through the hand above the ligament, the second end of the cutting element is introduced into the distal end of the needle and fed there through. Retraction of the needle leaves the cutting element in place for the transection.

The goal in implementing the methods disclosed in FIGS. 10A-J and paragraphs related thereto of the above-identified, co-pending application is for the physician to utilize a single introducer needle to enter the patient at a first location, traverse one side of the target tissue (ligament), and then exit the patient at a second location. This method creates a passageway through which the cutting element can be positioned (routed) relative to the target ligament for transection purposes. However, due to the sometimes complex anatomy of the patient, this is not always possible. For example, it is sometimes difficult to manipulate the introducer needle or router to exit the patient at the second location due to the presence of thick and stiff tissue mass that may make it almost impossible to exit the targeted second location in the patient. The shaft of the introducer needle has some flexibility and when the distal end of the shaft hits a hard tissue mass, the distal tip can be deflected away from the desired second location as it is further advanced within the patient. As a result of the presence and location of such hard tissue in the area where the procedure is being performed, the physician may not be able to properly position the distal tip of the introducer needle/router to exit the patient at the desired second location. Accordingly, there is a need for the physician to reach the second location with the needle/router without causing the distal tip to damage thick tissue located near the second location. The present invention provides alternative methods for creating the passageway needed to properly rout the cutting element about the target ligament when a hard, impassible tissue mass is encountered by the introducer needle.

Particular routing tools of the present invention enables the cutting element to be easily and quickly introduced and routed into position about the target ligament (or other structure to be dissected) with minimal disruption or trauma to the surrounding tissue. The routing tools may take the form of a pair of introducer needles which are utilized together in creating the passageway needed to rout the cutting element about the target ligament. A first hollow introducer needle is initially advanced into a first location on the patent adjacent to the target ligament. The first introducer needle is advanced past one side of the ligament until the distal end of the needle exits the patient at a second location. However, due to the presence of a hard tissue, the physician may not be able to advance the needle any further without either damaging tissue or pushing the distal tip of the needle to a location which is not the desired exit location. When this occurs, a second hollow introducer needle is inserted into the second location and advanced towards the distal tip of the first needle. The needles are dimensioned so that one of the lumens of the introducer needles receives the other introducer needle thereby creating a passage which runs one across one side of the target ligament and has an entry location and exit location on the patient. In this manner, the first introducer needle is used to create a first access port at a first location proximal to the target ligament and laterally adjacent thereto. The second introducer needle is then used to create a second access port at a second location just distal to the target ligament. The distal end of the introducer needle having the smaller diameter is then inserted into the larger lumen of the other introducer needle in vivo to create a passage across one side of the target ligament. The passage is then used to pass the cutting element therethrough to allow one end of the cutting element to extend from each of the access ports. The use of two introducer needles allows the physician to access the target ligament from two sides of the ligament, rather than one needle, which may make the creation of the passage across the target ligament easier to attain. The cutting element is extended through one end of the needle to the other end allowing approximately one half of the cutting element to be pulled from one end of the needle. The needle is then retracted from the patient to leave the cutting element in place such that a sizable portion thereof protrudes from both of the access port locations.

In another aspect of the present invention, the first introducer needle has a lumen sized to fit over the outer diameter of the shaft of the second introducer needle. Again, the first introducer needle is advanced through the first location as far as is safely possible. The smaller diameter shaft of the second introducer needle is then inserted into the patient at the desired second location and is advanced near the distal end of the first introducer needle. Imaging devices, such as an ultrasound device, commonly used for a variety of imaging applications, can be used to visualize the position of the distal ends of first and second introducer needles. The smaller diameter second introducer needle can then be placed inside of the lumen of the first introducer needle in vivo. The physician then advances the first introducer needle over the shaft of the second introducer needle and out of the second location on the patient. The second introducer needle can remain in vivo or it can be removed from the second location leaving only the first introducer needle extending from the first location, across a first side of the target ligament, and through the second location where its distal end will be located outside of the patient. This allows the cutting element to be passed through the lumen of the first introducer needle since both ends of the first introducer needle will now be located outside of the patient. Again, the cutting element is extended through one end of the needle to the other end allowing approximately one half of the cutting element to be pulled from one end of the needle. The first introducer needle is then retracted from the patient to leave the cutting element in place such that a sizable portion thereof protrudes from both of the access port locations.

In yet aspect of the present invention, the first introducer needle remains in vivo with the second introducer needle in order to create the passage for the cutting element. In another aspect of the invention, the first introducer needle can have the smaller diameter and can be introduced into a larger lumen of the second introducer needle. Again, the larger diameter shaft of the second introducer needle is inserted into the patient at the second location and is advanced near the distal end of the first introducer needle. An imaging device can be used to visualize the position of the distal ends of first and second introducer needles. The first introducer needle is then advanced through the lumen of the second introducer needle and through the access port at the second location. The second introducer needle can remain in vivo or it can be removed from the second access port leaving only the first introducer needle extending from the first access port, across a first side of the target ligament, and through the second access port where its distal end will be located outside of the patient. This allows the cutting element to be passed through the lumen of the first introducer needle since both ends of the first introducer needle are now located outside of the patient. The cutting element is extended through one end of the needle to the other end allowing approximately one half of the cutting element to be pulled from one end of the needle. The needle is then retracted from the patient to leave the cutting element in place such that a sizable portion thereof protrudes from both of the access port locations.

In another aspect of the present invention, the first introducer needle is advanced transverse to one side of the target ligament until it can no longer be safely advanced within the patient. The second introducer needle having a smaller diameter which fits within the lumen of the first introducer needle is then introduced into the lumen. The second introducer needle is initially inserted into the second location on the patient and is inserted into the lumen of the first needle while both needles remain in vivo. The second introducer needle can then be advanced through the lumen of the first introducer needle so that its distal end will extend through the first location and outside of the patient. The second introducer needle will now be extending from the second location, across a first side of the target ligament, and through the first location where its distal end will be located outside of the patient. This allows the cutting element to be passed through the lumen of the second introducer needle (with or without the first introducer in place) since both ends of the second introducer needle will now be located outside of the patient creating a direct passage (the needle's lumen) for the physician to advance the cutting element therethrough. The cutting element is extended through one end of the second introducer needle to the other end allowing approximately one half of the cutting element to be pulled from one end of the needle. The second introducer needle is then retracted from the patient to leave the cutting element in place such that a sizable portion thereof protrudes from both access port locations.

The methods described above reflect methods and components which can be utilized in the described methods for accessing one side of a target ligament. Further methods for positioning the cutting element around the target ligament include creating a passage on the opposite side (second side) of the target ligament to allow the cutting element to be wrapped or looped about the target ligament for transection. Two introducer needles may be required to access the second or opposite side of the target ligament in the presence of hard tissue on the opposite side of the ligament. The same methods described above for routing the first and second introducer needles across the first side of the target ligament also could be used to advance the needles past the second side of the target ligament. In one particular aspect, either the first introducer needle or the second introducer needle will be routed across the second side of the ligament depending upon which method is used to transverse the side of the target tissue. In this manner, the two introducer needles cooperate to allow one of the needles to traverse the second side of the ligament and extend from both the first and second access locations. Alternatively, both first and second introducer needles could be used to create a single passageway by connecting the lumens of the needles (described above) is utilized. One end portion of the cutting element can then be fed into an end of the hollow needle positioned across the second side of the ligament and is advanced outside of the needle. Both end portions of the cutting element will now be extending either out of the first or second location access port. The routing of the cutting element about the ligament is thereby complete leaving the cutting element in position for the transection.

It should be appreciated that the physician could interchangeably use any of the alternative methods for advancing the first and second introducer needles along the first and second sides of the target ligament as described above when hard tissue is encountered.

The physical characteristics of the cutting element are selected to facilitate a kerf-less cut through the ligament. In this regard, the cutting element is non-abrasive to prevent the cutting element from abrading or cutting any tissue surrounding the target ligament. The small diameter and high tensile strength of the cutting element provides for the transection of the ligament by the manipulation of the ends of the cutting element. Unequal forces can alternatingly be applied to the two ends of the cutting element to induce a reciprocating cutting action. Alternatively, one end can be pulled with greater force than the other element so as to pull the cutting element in a single direction as it cuts through the ligament. As a further alternative, both ends can be pulled simultaneously with equal force to simply pull the cutting element through the ligament. The substantially smooth, none abrasive surface of the cutting element causes a knife-like cut to be achieved without the formation of a kerf and thus without an attendant deposition of detached material in and about the surgical site. Reciprocation may preferably be achieved with the use of a power tool, by which the two ends of the cutting element are alternating pulled. A stiffened section one or both ends of the cutting element facilitates the introduction of the cutting element into the hollow introducer needle.

The very small cross-section of the routing tool, whether it takes the form of the hollow introducer needle or the hooked retrieval needle, and of the cutting element, as well as minimally invasive method by which such hardware is introduced and positioned within the hand greatly reduces the risk of injury to the median nerve as well as to the smaller nerves that branch out therefrom. Additionally, the fact that the cutting element is positioned via only two tiny punctures and that the transection is performed via only one of those punctures, recovery time is minimal and scaring is essentially negligible.

The invention can additionally be modified in order to further simplify the surgical procedure. For example the sequence of steps can altered in the routing of the cutting element about the ligament such that the routing tool is first extended across the top of the ligament before the tool is subsequently extended through the carpal tunnel for the routing of the cutting element about the ligament. Additionally, a rigid alignment tool may be attached to the second end of the cutting element to facilitate engagement of the cutting element by the hooked retrieval needle embodiment of the routing tool component at a location completely within the hand and thus much closer to the distal edge of the ligament in order to minimize the transection of any tissue adjacent to the ligament. A retrieval needle may further be marked so as to allow the rotational orientation of the hooking element to be ascertained while within the hand and thereby enhance the ability to engage the cutting element. Additionally, a protective sleeve about a portion of the cutting element may be employed to protect tissue located between the proximal entry port and the ligament. Both ends of the cutting element may be caused to extend through a single sleeve or each end may be caused to extend about its own protective sleeve.

These and other advantages of the present invention will become apparent from the following detailed description of preferred embodiments which, taken in conjunction with the drawings illustrate by way of example the principles of the invention.

BRIEF DESCRIPTION OF THE DRAWINGS

FIGS. 10A-J are cross-sectional views of the hand with a revealed transverse carpal ligament illustrating a preferred sequence of steps for practicing the method of the present invention using a hollow introducer needle as the routing tool component;

FIGS. 13A-D are cross-sectional views of the hand with a revealed transverse carpal ligament illustrating a preferred sequence of practicing a method of the present invention of placing a cutting element transverse to the target ligament along a first (bottom) side using hollow introducer needles as the routing tool component;

DETAILED DESCRIPTION OF THE PREFERRED EMBODIMENTS

The present invention provides for the minimally invasive transection of tissue and obviates the need for scalpels, saws or endoscopes. The invention is especially applicable for the transection of ligaments and most particularly, for the release of the transverse carpal ligament in the treatment of carpal tunnel syndrome.

Figure 1:
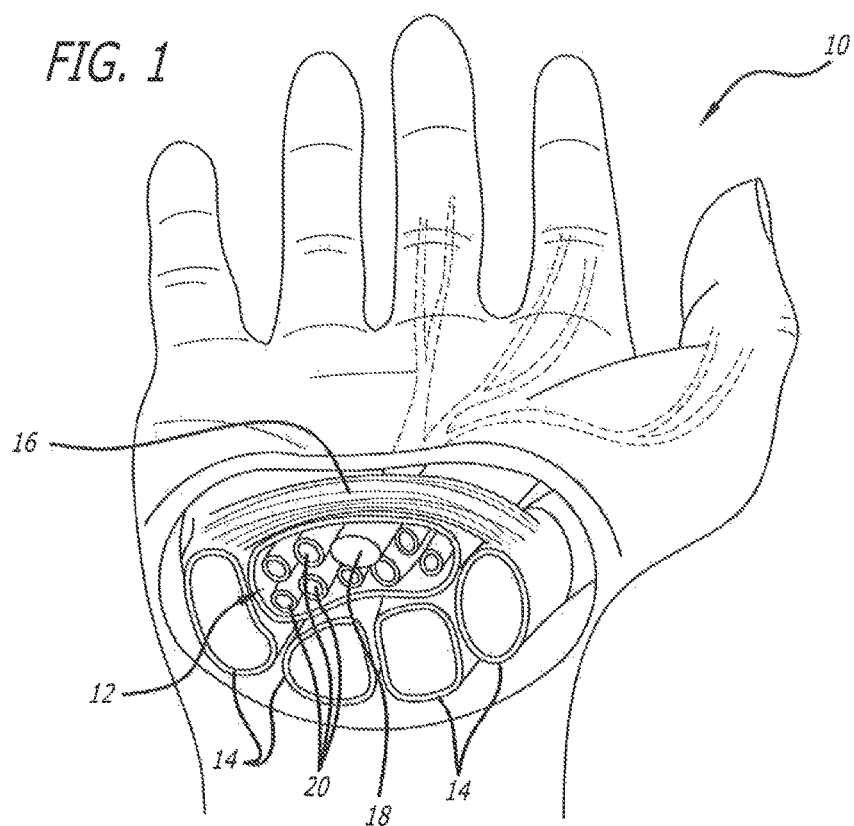
FIG. 1 is a cross-sectional view of the carpal tunnel area of the hand.

FIG. 1 is a cross-sectional view of the carpal tunnel area of the hand 10. The carpal tunnel 12 is the area of the wrist and palm of the hand 10 formed by a U-shaped cluster of bones 14 that form a hard floor and two walls of the tunnel. The roof of the tunnel is formed by the transverse carpal ligament 16 which attaches to the wrist bones. Within the confines of the tunnel is the median nerve 18 and the flexor tendons 20 of the thumb and fingers. Carpal tunnel syndrome is caused by a compression of the median nerve by either a decrease in the size of the tunnel or an increase in the size of its contents. Such pressure may be relieved by a release of the ligament such as by a transection thereof.

Figure 2:
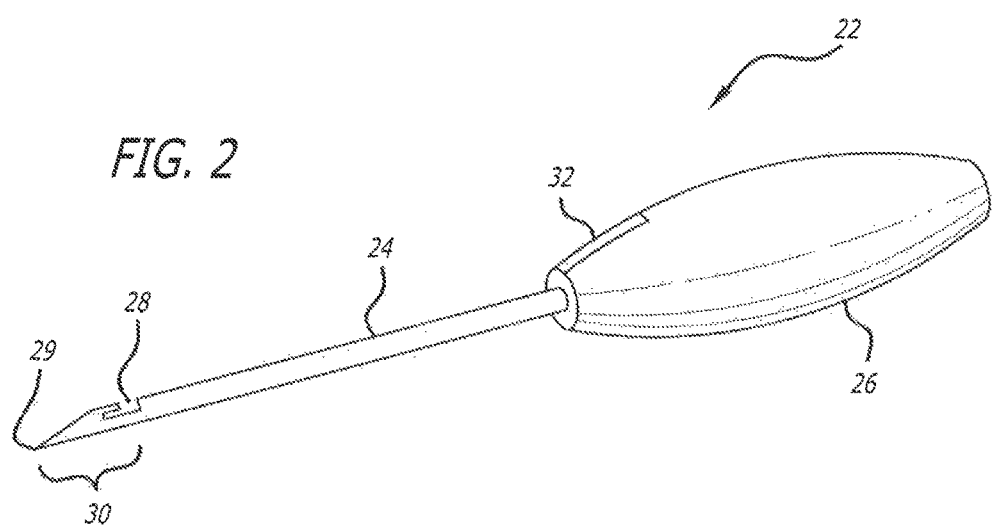
FIG. 2 is a perspective view of a preferred embodiment of the routing tool component of the present invention in the form of a hooked retrieval needle.

FIG. 2 is perspective view of a preferred embodiment of the routing tool of the present invention wherein such tool takes the form of a hooked retrieval needle 22. The tool generally includes a thin, rigid and elongated distal section 24 and a handle 26 at its proximal end. The distal section has hooking element 28 disposed near its distal end 30. The hooking element is preferably defined by a void formed within the outer diameter of the elongated distal section of the retrieval tool so as to present a substantially smooth outer surface and thereby minimize the potential for trauma as the tool is extended into or retracted from tissue. The distal end may have a sharp tip 29 as is shown in the illustrated embodiment. Alternatively, the tip may have a more blunted configuration. The hooking element is spaced slightly back (reference numeral 30) from the distal end. A marking 32 on the handle may be included demarking the rotational position of the hook-like feature near the tool's distal end. The length of the distal section is selected to be greater than the width of the transverse carpal ligament. Its diameter is selected to be no greater than about 1 mm.

Figure 3:
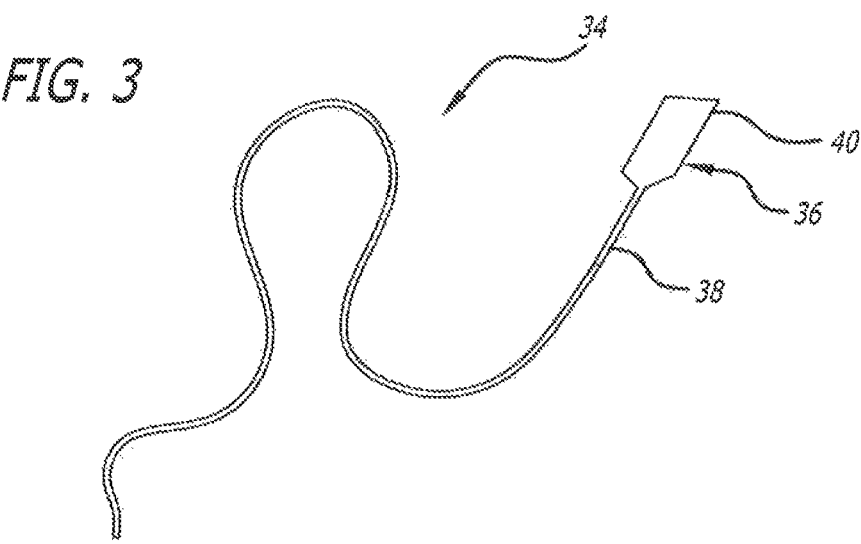
FIG. 3 is a perspective view of a preferred embodiment of the cutting element of the present invention.

FIG. 3 is a perspective view of the cutting element 34 of the present invention with the optional locator tool 36 attached thereto. The cutting element has a flexible, small diameter, thread-like structure with a high tensile strength and a smooth surface, preferably with an average surface roughness no greater than 50 micrometers. The cutting element may comprise a monofilament or a plurality of braided or otherwise joined fibers or strands wherein each strand has a smooth surface so as to present a relatively smooth, none-abrasive surface. Its physical characteristics include a bend radius of less than half the thickness of the ligament and preferably a zero bend radius, a diameter of less than about 1.0 mm, and a breaking strength of over 2 lbs. The cutting element may comprise fiber or yarn formed of cotton, silk, glass fiber, carbon fiber, various plastic fibers or metal. More particularly, textile fiber, synthetic fiber, mineral fiber, polymer fiber, microfibers may be used. The optional locator tool includes a rigid distal end 38 of a diameter sufficiently small to be extended into the access port and to be captured within the hooking element 28 of the retrieval tool 22. A handle 40 is disposed near its proximal end to enable the tool to be grasped and manipulated.

Figure 4A:
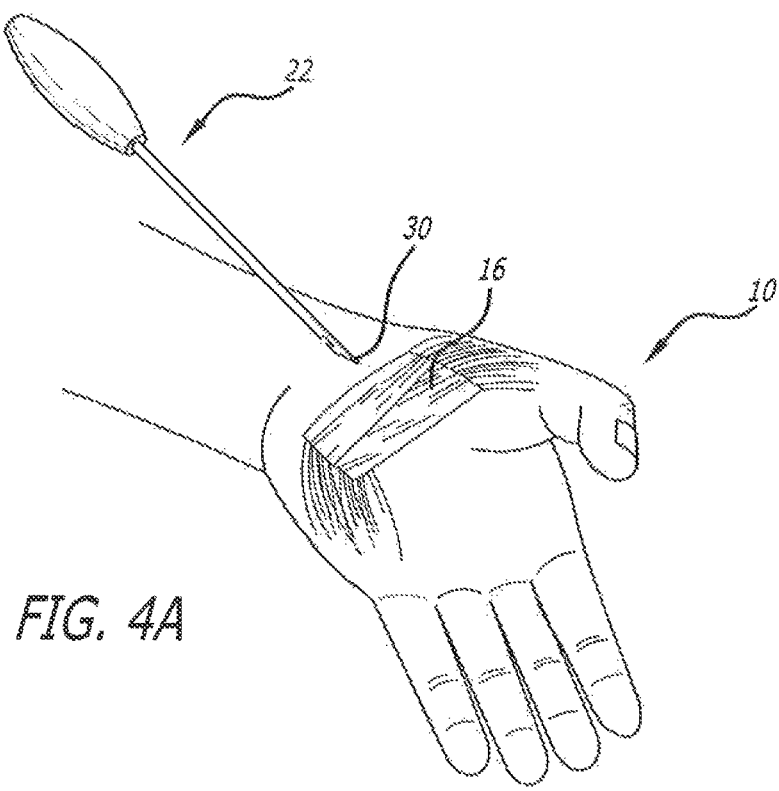
FIGS. 4A-H are cross-sectional views of the hand with a revealed transverse carpal ligament illustrating a preferred sequence of steps for practicing the method of the present invention using a hooked retrieval needle as the routing tool component.

FIGS. 4A-4H illustrate a preferred method of practicing the present invention. After anesthetizing the area of the hand 10 near and about the transverse carpal ligament 16, the distal end 30 of the retrieval needle 22 is brought into contact with the hand just proximal to the proximal edge of the target ligament as is shown in FIG. 4A. The ligament is visible in the Figures for purposes of clarity only as no incision is made throughout the entire procedure to in any way expose the ligament to view. Additionally, an imaging device, such as an ultrasound device, such as is commonly used for a variety of imaging applications, is used to visualize the position of the retrieval needle relative to the ligament but is not shown so as not to obscure the surgical site again for purposes of clarity. It is preferable to enter the hand at a position about 30 mm proximal of the proximal edge of the transverse carpal ligament as the carpal tunnel can then be entered at a shallower angle obviating the need to adjust the angle of the needle after the tunnel has been reached and thereby minimizing trauma to tissue in addition to allowing the retrieval needle to be more easily imaged.

Figure 4B:
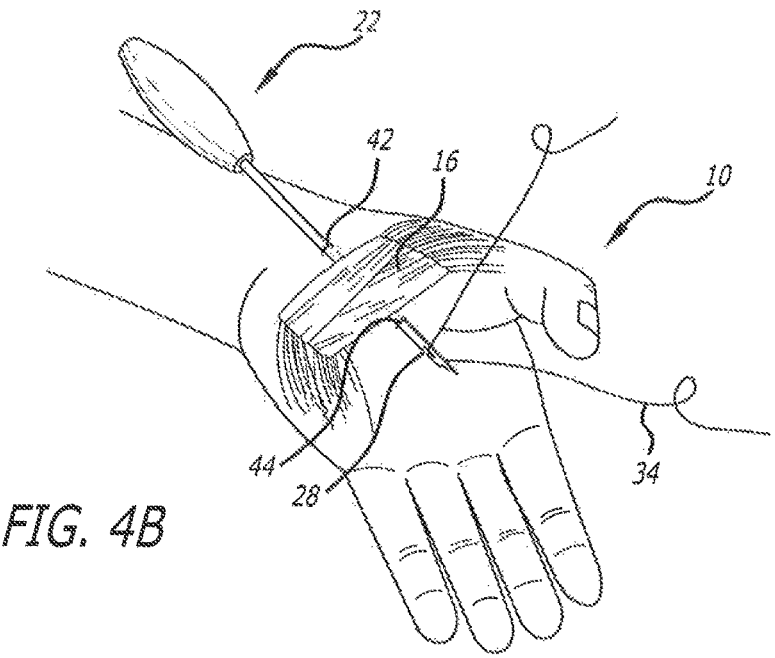

In FIG. 4B, the retrieval needle has been advanced into the hand via entry port 42, through the carpal tunnel just under the ligament and out through exit port 44. The entry and exit ports may be formed by the direct extension of the retrieval needle through the skin in the event the retrieval needle 22 is selected to have a sharp distal tip 29. In the event a retrieval tool is used with a blunt tip, a sharp instrument is necessary for forming the access ports and guide the retrieval tool into the hand. The Figure additionally shows the cutting element 34 having been engaged in the hooking element 28 near the tool's distal end. In this particular embodiment, the cutting element is devoid of a locator tool attached to its distal.

Figure 4C:
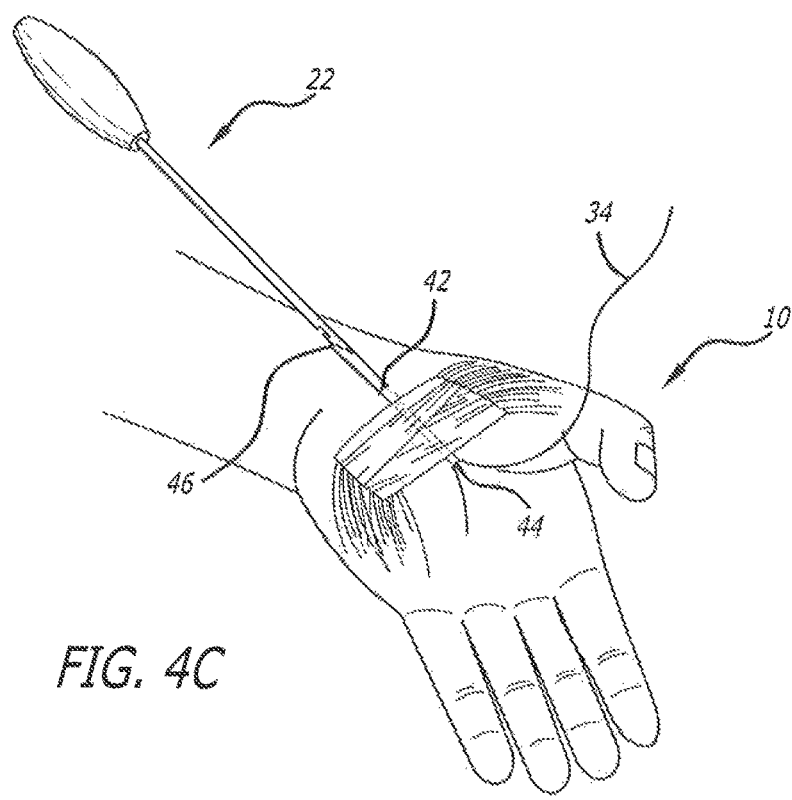
Figure 4D:
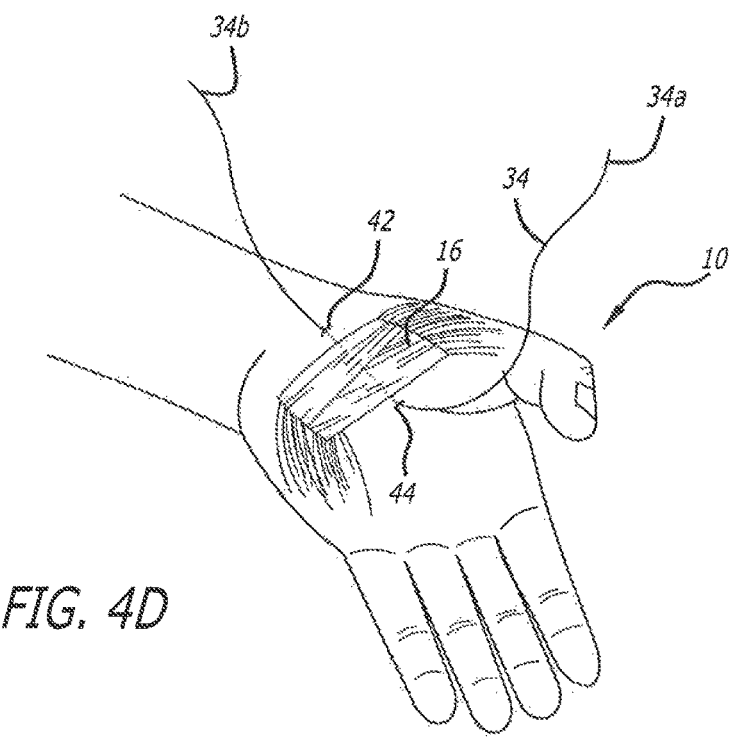

Once the cutting element 34 is engaged, the retrieval needle 22 is retracted from the hand so as to draw a loop 46 of the cutting element into the hand via port 44, through the carpal tunnel and out of entry port 42 as is shown in FIG. 4C. The loop is then disengaged from the retrieval needle and while one end of the cutting element 34a is restrained, the loop is pulled so as to draw the opposite end 34b of the cutting element free of the hand as is shown in FIG. 4D.

Figure 4E:
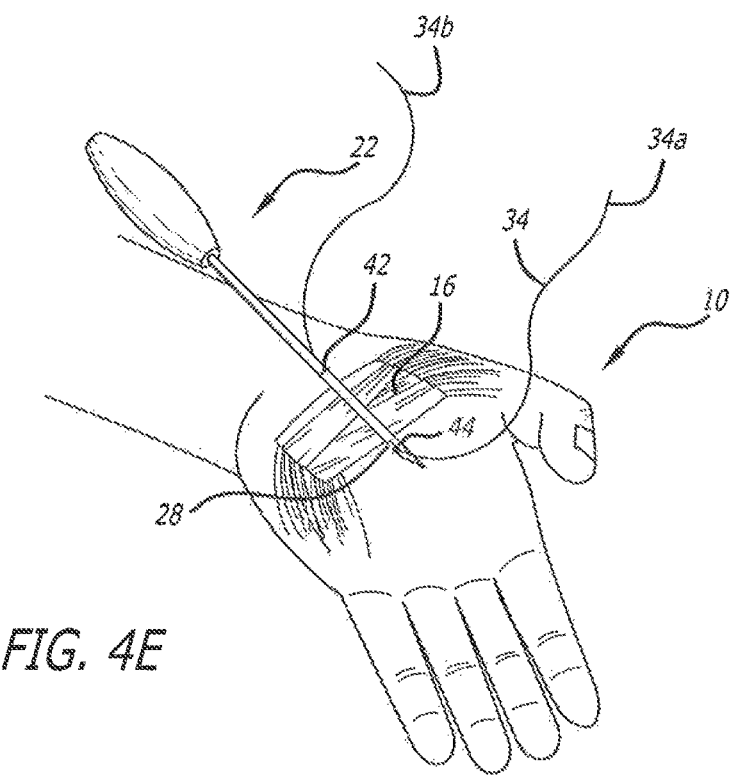

FIG. 4E illustrates the subsequent step of the method wherein the retrieval needle 22 is readvanced into the hand via access port 42, is guided across the top surface of ligament 16 to remerge from the hand via access port 44. The section of cutting element 34 extending from under the ligament is engaged with the hooking element 28 of the retrieval needle.

Figure 4F:
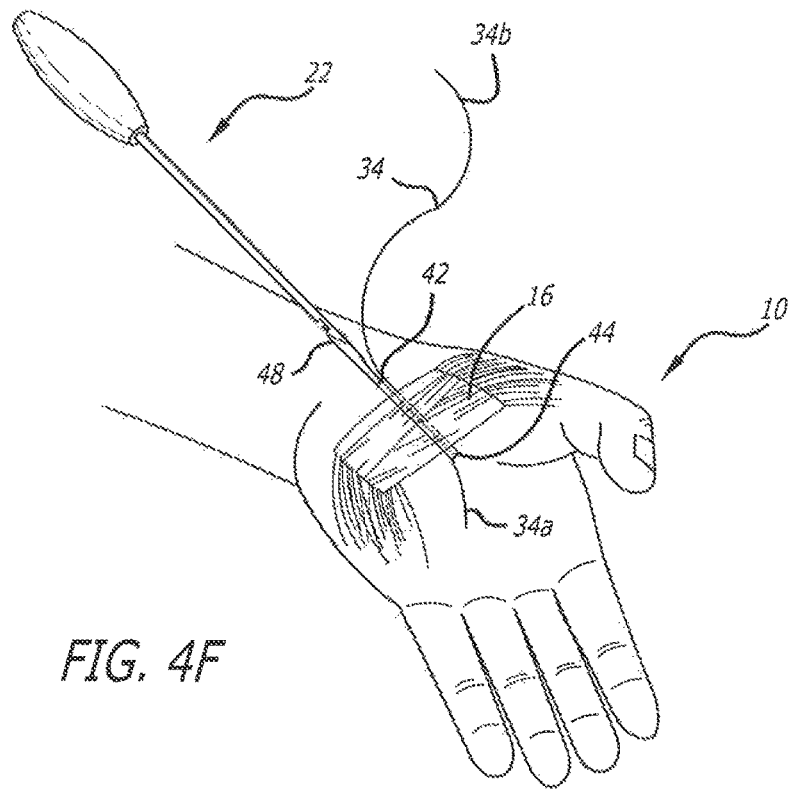
Figure 4G:
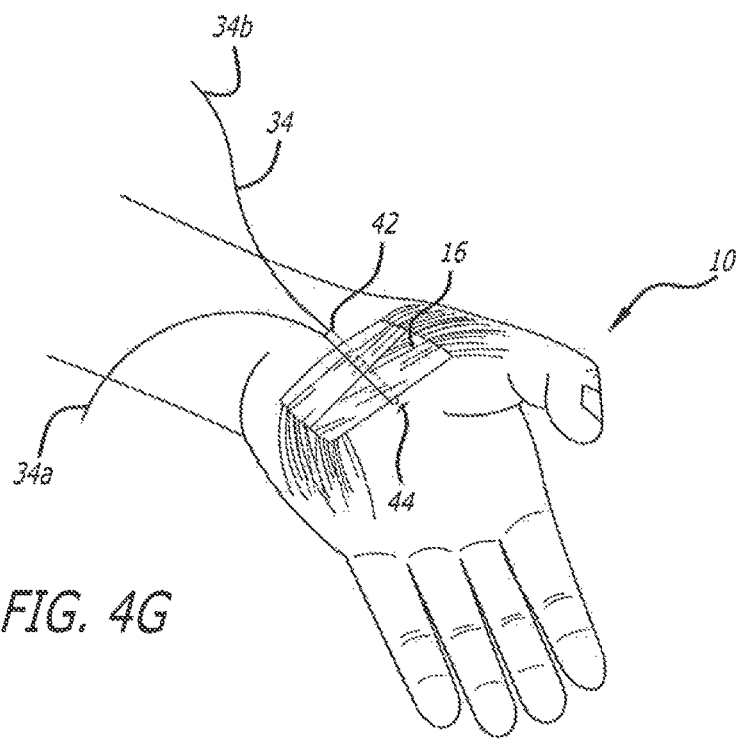
Figure 4H:
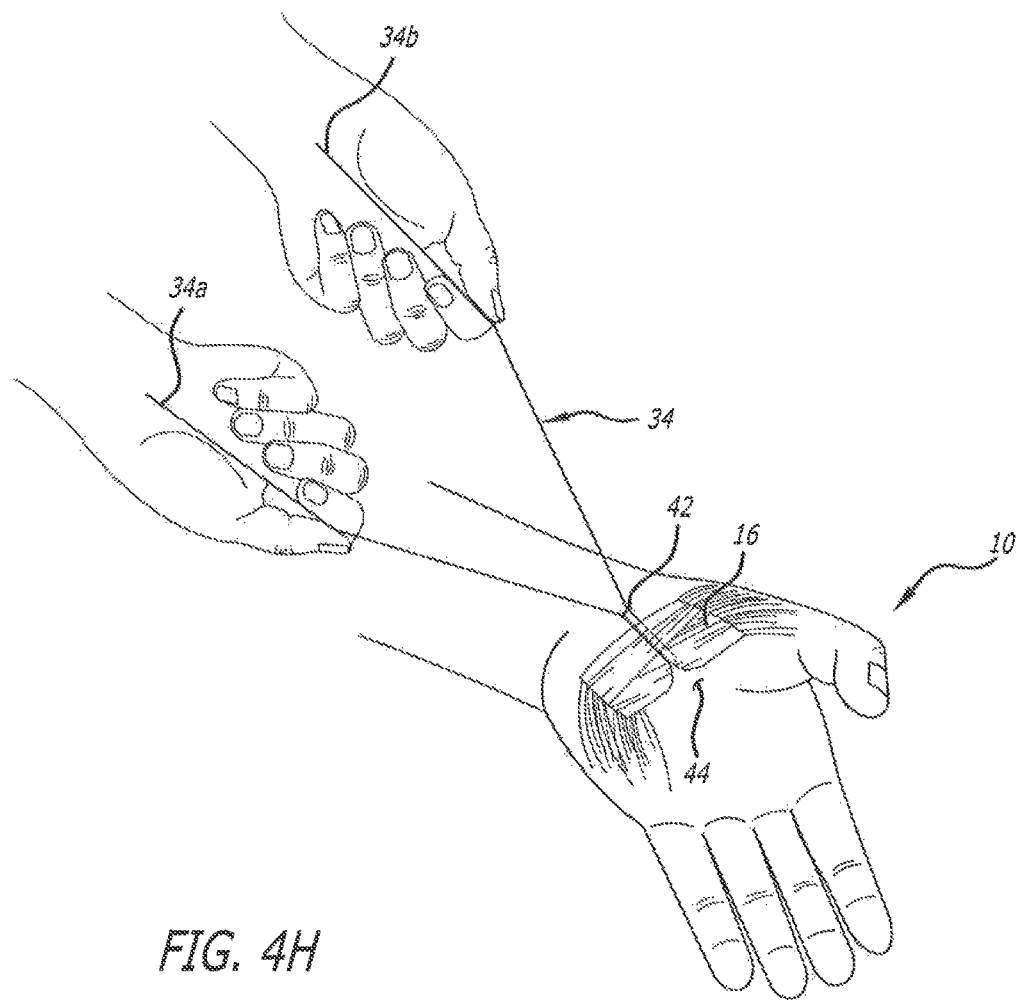

Once the cutting element 34 is again engaged, the retrieval needle 22 is retracted from the hand so as to draw a loop 48 of the cutting element into the hand via port 44, through the carpal tunnel and out of entry port 42 as is shown in FIG. 4F. The loop is then disengaged from the retrieval needle and while end 34b of the cutting element is restrained, the loop is pulled so as to draw the end 34a of the cutting element free of the hand as is shown in FIG. 4G. The cutting element is thereby in position about ligament 16 for subsequent manipulation to effect the transection. As is shown in FIG. 4H, the ends 34a, 34b of the cutting element may simply be grasped by the user, may be wound around the hands or fingers of the user for a firmer grip or alternatively, may be fitted with handles to provide for maximum grip and control. Unequal forces can alternatingly be applied to the two ends of the cutting element to induce a reciprocating cutting action either by hand or with the use of an appropriately configured power tool. Alternatively, one end can be pulled with greater force than the other element so as to pull the cutting element in a single direction as it cuts through the ligament. As a further alternative, both ends can be pulled simultaneously with equal force to simply pull the cutting element through the ligament. When transection has been achieved, the cutting element is simply withdrawn through access port 42. Application of a small bandage over each of the access ports 42, 44 completes the procedure.

Figure 5A:
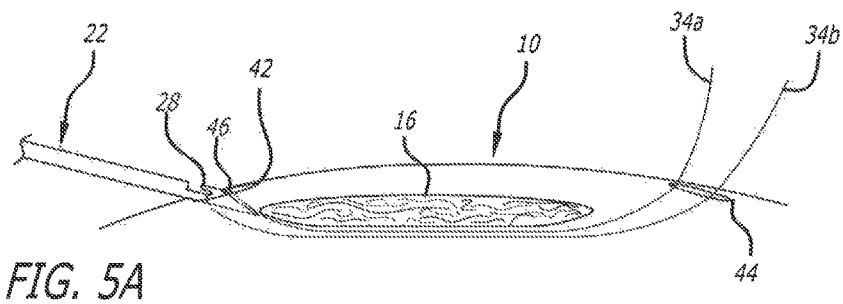
FIGS. 5A-C are cross-sectional views of the hand and the transverse carpal ligament illustrating alternative preferred steps for practicing the method of the present invention.

In an alternative embodiment, and as a modification to the step shown in FIG. 4C, the retrieval needle 22 is not completely withdrawn from access port 42 as illustrated in FIG. 5A. The needle is retracted just enough to expose the hooking element 28 and allow the loop 46 of the cutting element 22 to be disengaged and withdrawn, while most of the distal end 30 remains below the skin. As a result, it is more likely that the needle will follow the same pathway to the ligament 16 before traversing its top surface resulting in less trauma and disruption to intervening tissue both while advancing the needle as well as at the completion of the transection step.

Figure 5B:
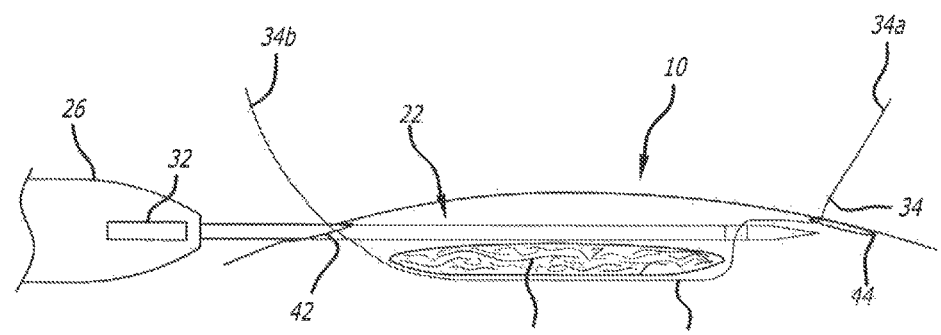

In another alternative embodiment, and as a modification of the step shown in FIG. 4E, the retrieval needle 22 is not extended through port 44 to engage cutting element 34 as is illustrated in FIG. 5B. Rather the cutting element is engaged within the hand, preferably as close to possible to the distal edge of the transverse carpal ligament 16. The needle is shown with its hooking element rotated toward the viewer. The marking 32 on the handle 26 allows the user to ascertain the rotational orientation of the hooking element without a direct view of the distal end of the retrieval needle. By engaging the cutting element 34 closer to the distal edge of the ligament before drawing it across the top surface of the ligament, less extraneous tissue is apt to be captured between the cutting element and the ligament and thus less trauma thereto will be caused during the transection of the ligament.

Figure 5C:
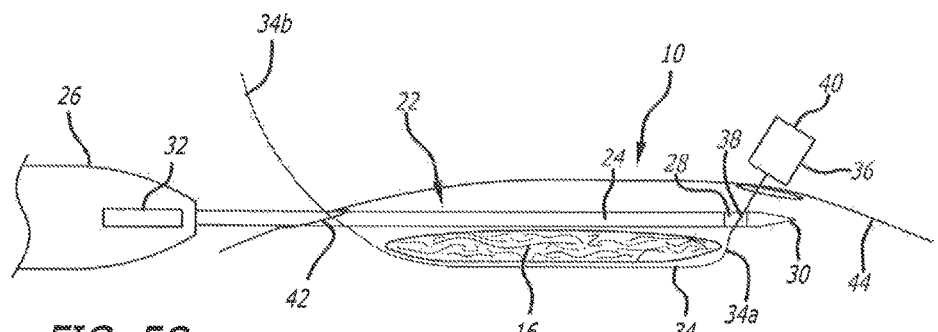

As a further alternative to the preferred embodiment shown in FIG. 5B, FIG. 5C illustrates the step using the cutting element 34 having the locator tool 40 attached thereto. Once the distal end 30 of the tool is in position such that the hooking element is located just distal of the distal edge of the transverse carpal ligament as confirmed by the ultrasound image, the cutting element 34 is pulled from the end 34b projecting from access port 42 so as to draw its opposite end 34a and the locator tool that is attached thereto into access port 44. Once the locator tool is extended to the approximate depth that is illustrated, the ability to more readily engage the retrieval needle is enhanced by virtue of the locator tool's visibility under ultrasound imaging and by virtue of the tactile feedback that is provided when contact is made between the rigid distal section 24 of the retrieval needle and the rigid distal end 38 of the locator tool. Once engagement with the hooking element 28 of the retrieval needle is confirmed, the locator tool is withdrawn from access port 44, leaving the cutting element in place within the hooking element. Subsequent retraction of the retrieval needle causes a loop of the cutting element to be drawn through the pathway above the ligament and out of access port 42. Severing the cutting element from the locator tool allows the free end 34*a* of the cutting element to be drawn through the hand and out of the access port to complete the routing of the cutting element about the target ligament.

In the event a cutting element 34 is selected that has a larger than zero bend radius, it may be desirable to first introduce a zero bend radius pilot thread into the hand and position it about the ligament in the manner as was described above with regard to placement of the actual cutting element. Once such pilot thread is in place, one end is attached directly to one end of the cutting element and simply pulled through so as to replace the pilot thread with the cutting element. Such approach allows the size of the access ports to be minimized that would otherwise have to be enlarged in order to accommodate the larger loops 46, 48 that are formed by a cutting element having a non-zero bend radius.

Figure 6A:
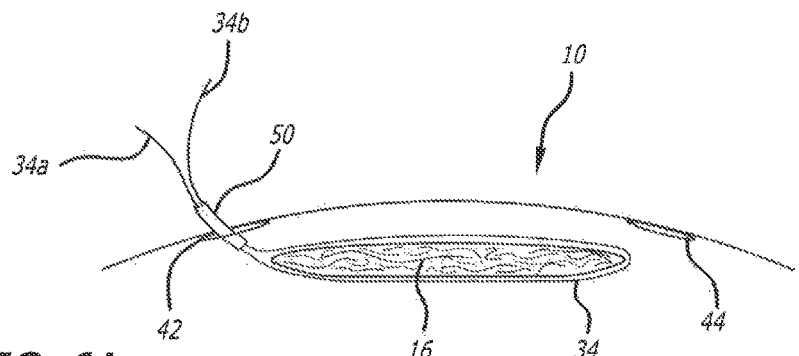
FIGS. 6A and B are cross-sectional views of the hand and the transverse carpal ligament illustrating an alternative preferred embodiment in which protective tubes are used.
Figure 6B:
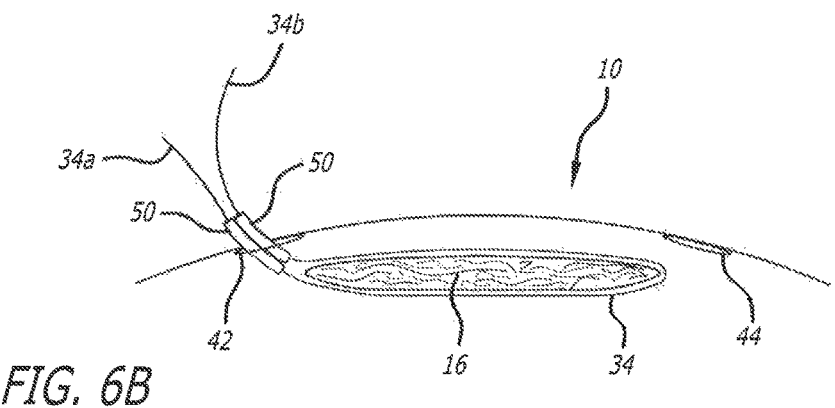

A further alternative preferred method of practicing the present invention includes the use of protective tube or tubes 50 that are positioned about the cutting element at access point 42 as is illustrated in FIGS. 6A and B. Both ends of the cutting element may be passed through a single tube (FIG. 6A) or each end may be passed through its own tube (FIG. 6B). The tube or tubes serve to protect the surrounding tissue from injury as tension is applied to the cutting element and it is drawn or reciprocated to effect the transection. The tubes are especially effective when the cutting element undergoes some curvature in and about access point 42. The thin-walled tubing is selected to be flexible but resistant to being cut by the cutting element.

Figure 7A:
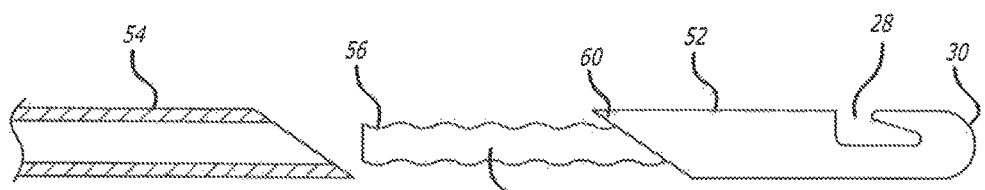
FIGS. 7A and 7B are greatly enlarged cross-sectional views of an alternative preferred embodiment of the hooked retrieval needle.
Figure 7B:
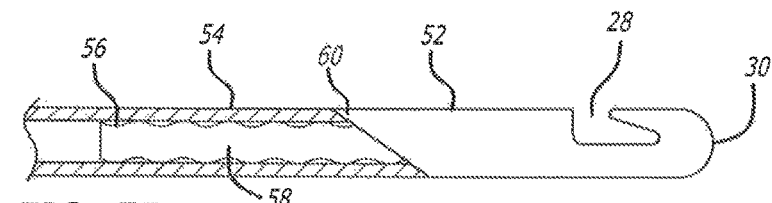

In another alternative preferred embodiment, a modified retrieval tool 52 is configured for capture within a hypodermic needle 54 as is shown in FIGS. 7A and 7B. The hypodermic needle is initially used to form access port 42, to inject anesthetic and/or a liquid, such as saline solution, to inflate the surgical site so as to separate the various tissues and components to provide easier access for routing the cutting element into place. After the injection is complete, the hypodermic needle is extended out of the body to form access port 44. The specially configured blunt tipped retrieval tool is inserted into the hypodermic needle and locked into place (FIG. 7B) via locking mechanism 56. Such locking mechanism may take any of various forms including the interference fit that is created by the slightly wavy configuration of the shank 58 that is shown in the Figure. After the cutting element is engaged by the hooking element 28 of the retrieval tool, the hypodermic needle is retracted to draw loop 46 into the hand as is shown in FIG. 4C. The distal section 60 of the retrieval tool 52 may have its outer diameter selected to substantially match the outer diameter of the hypodermic needle to create a smooth transition.

Figure 8:
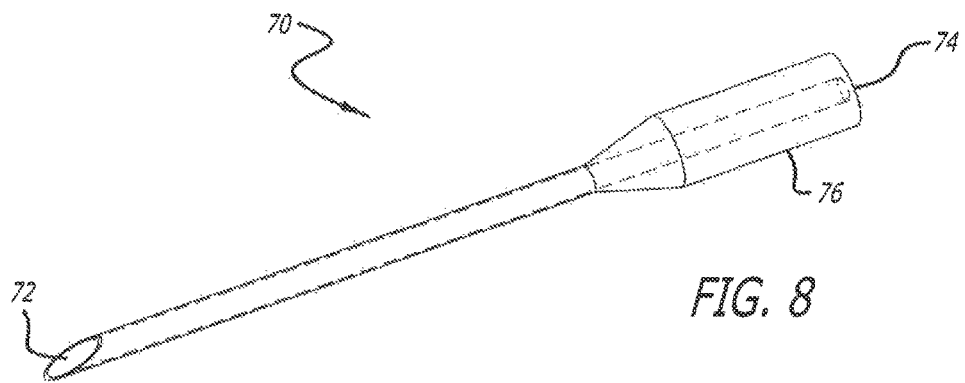
FIG. 8 is a perspective view of another preferred embodiment of the routing tool component of the present invention in the form of a hollow introducer needle.

FIG. 8 is perspective view of another preferred embodiment of routing tool component of the present invention wherein the tool takes the form of a hollow introducer needle 70. The hollow needle includes a sharp or blunt distal end 72 and has hollow interior extending from its distal end to its proximal end 74. A handle 76 may be disposed about its proximal section to facilitate its manipulation. The length of the section of introducer needle distal to the handle is selected to be greater than the width of the target transverse carpal ligament. Its diameter is selected to be no greater than about 2 mm.

Figure 9:
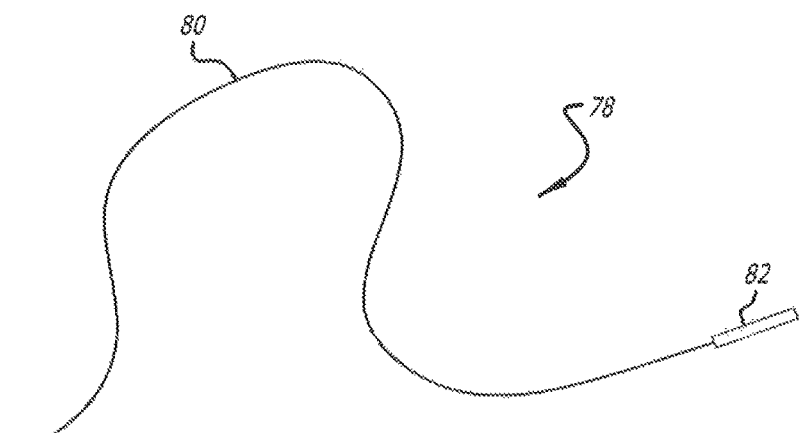
FIG. 9 is a perspective view of another preferred embodiment of the cutting element of the present invention.

FIG. 9 is a perspective view of a preferred embodiment of the cutting element 78 of the present invention. Substantially the entire length 80 of the cutting element has a flexible, small diameter, thread-like structure with a high breaking strength and a smooth surface, preferably with an average surface roughness no greater than 50 micrometers. The cutting element may comprise a monofilament or a plurality of braided, twisted or otherwise joined fibers or strands wherein each strand has a smooth surface so as to present a relatively smooth, none-abrasive surface. Its physical characteristics include a bend radius of less than half the thickness of the ligament and preferably a zero bend radius, a diameter of less than about 1.0 mm, and a breaking strength of over 2 lbs. The cutting element may comprise fiber or yarn formed of cotton, silk, glass fiber, carbon fiber, various plastic fibers or metal. More particularly, textile fiber, synthetic fiber, mineral fiber, polymer fiber, microfibers may be used. At least one end of the cutting element has a stiffened section 82 to facilitate the introduction into and the extension through the hollow introducer needle 70. The stiffened section may be formed by covering the section with relatively stiff tubing, by subjecting a synthetic fiber to heat, by the infusion of for example a resin or by the attachment of for example a suture needle. The stiffened section 82 preferably has a diameter less than the inner diameter of the introducer needle. The enhanced diameter shown in the drawing is for illustration purposes only.

Figure 10C:
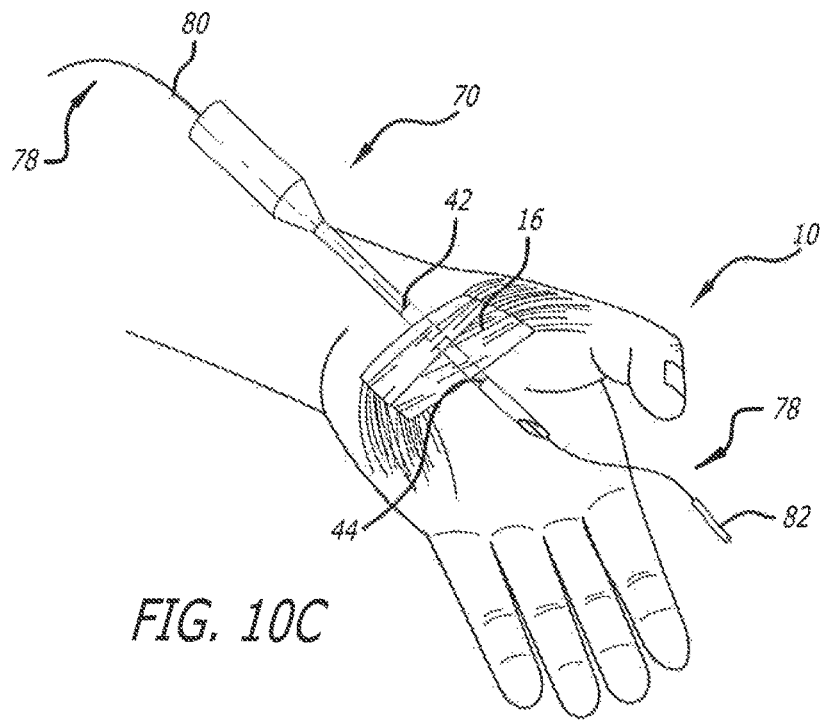

FIGS. 10A-J illustrate a preferred method of practicing the present invention. After anesthetizing the area of the hand 10 near and about the transverse carpal ligament 16, the distal end 72 of the hollow introducer needle 70 is brought into contact with the hand just proximal to the proximal edge of the target ligament as is shown in FIG. 10A. The ligament is visible in the Figures for purposes of clarity only as no incision is made throughout the entire procedure to in any way expose the ligament to view. Additionally, an imaging device, such as an ultrasound device, such as is commonly used for a variety of imaging applications, is used to visualize the position of the introducer needle relative to the ligament but is not shown so as not to obscure the surgical site again for purposes of clarity. It is preferable to enter the hand at a position about 30 mm proximal of the proximal edge of the transverse carpal ligament as the carpal tunnel can then be entered at a shallower angle obviating the need to adjust the angle of the needle after the tunnel has been reached and thereby minimizing trauma to tissue in addition to allowing the introducer needle to be more easily imaged.

In FIG. 10B, the introducer needle has been advanced into the hand via entry port 42, through the carpal tunnel just under the ligament and out through exit port 44. The entry and exit ports may be formed by the direct extension of the introducer needle through the skin. The Figure additionally shows the cutting element 78 being advanced toward the proximal opening of introducer needle wherein the stiffened section 82 of the cutting element serves to facilitate the threading of the cutting element into the needle's hollow interior.

Figure 10D:
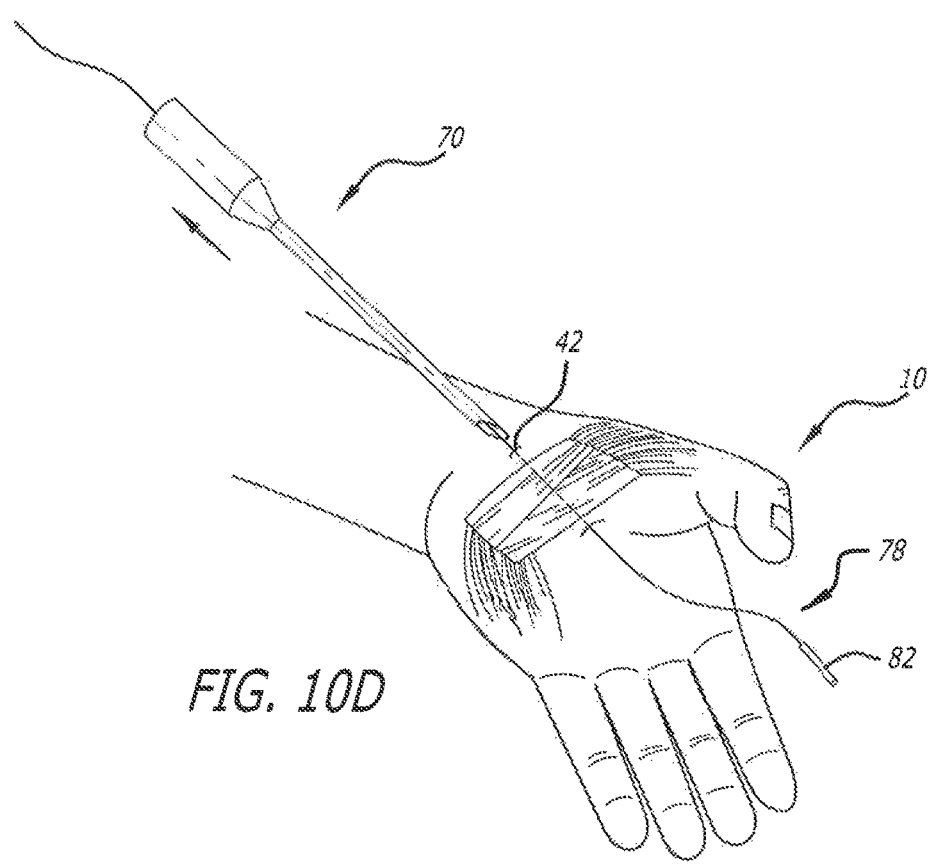
Figure 10E:
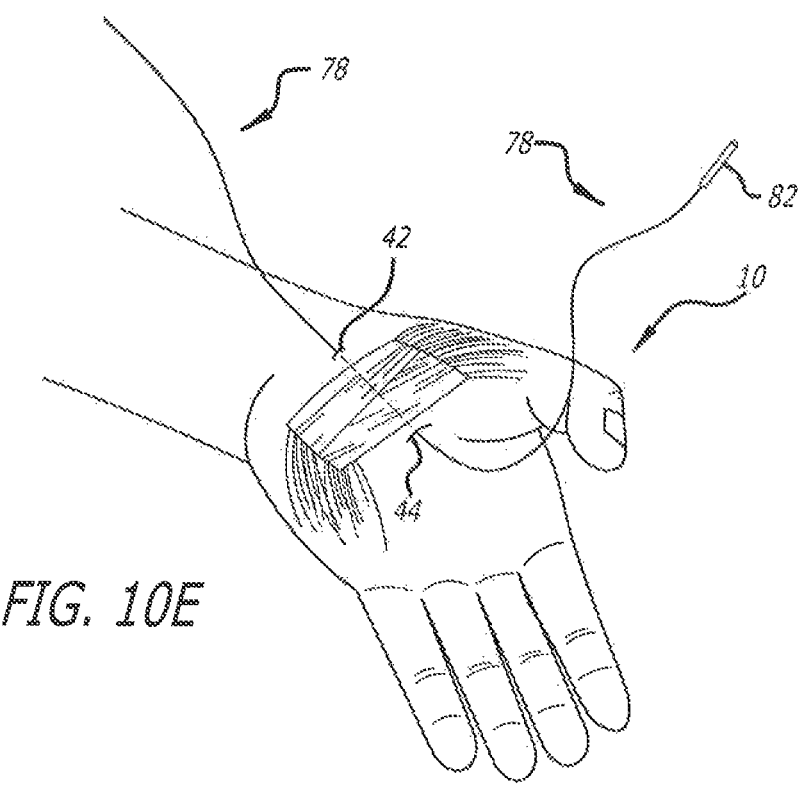

FIG. 10C shows the cutting element emerging from the introducer needle's distal end while FIG. 10D illustrates the subsequent retraction of the needle to leave the cutting element in place as is shown in FIG. 10E. As such, a section of cutting element 78 is left projecting from entry port 42 and from access port 44 while its central section extends through the carpal tunnel just below the transverse carpal ligament 16.

Figure 10F:
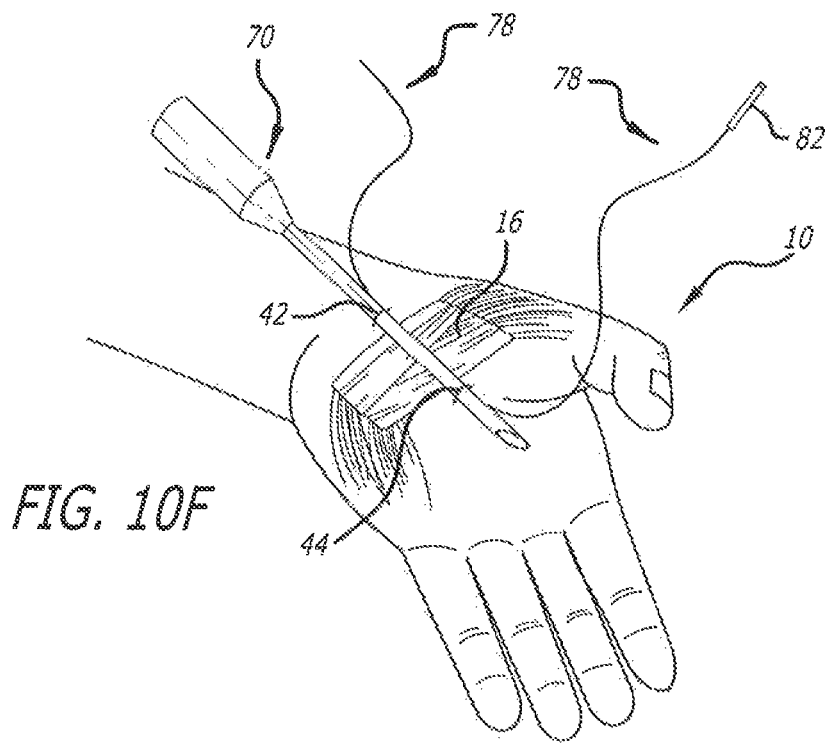
Figure 10G:
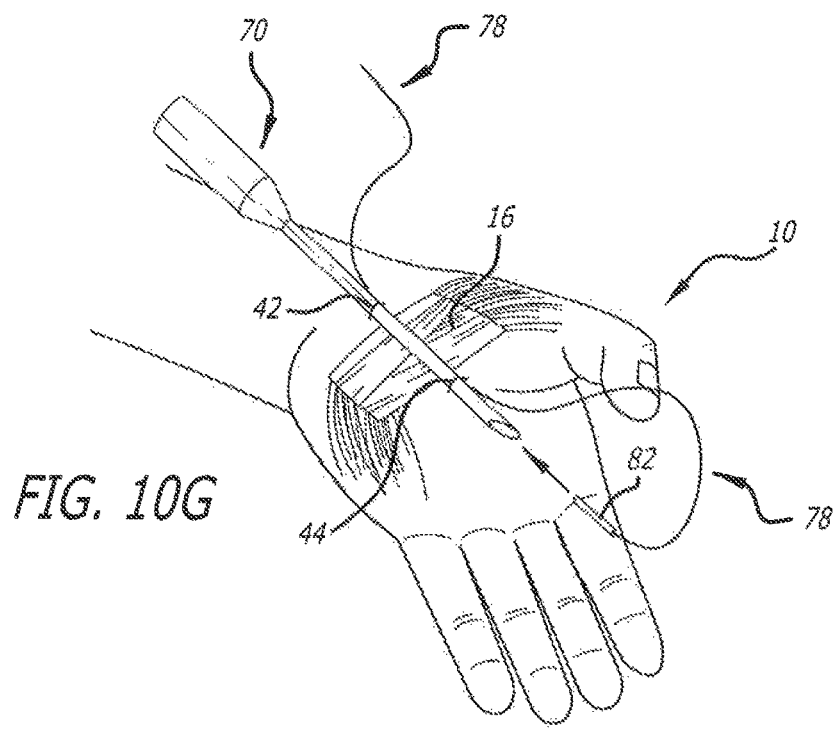

FIG. 10F illustrates the subsequent step of the method wherein the introducer needle has been reintroduced into the hand via entry port 42 immediately adjacent to the placed cutting element 78. The introducer needle has been advanced through the hand immediately above the transverse carpal ligament 16 to reemerge from access port 44. Alternatively, the introducer needle may be reintroduced into the hand via access port 44 to reemerge from port 42.

Figure 10H:
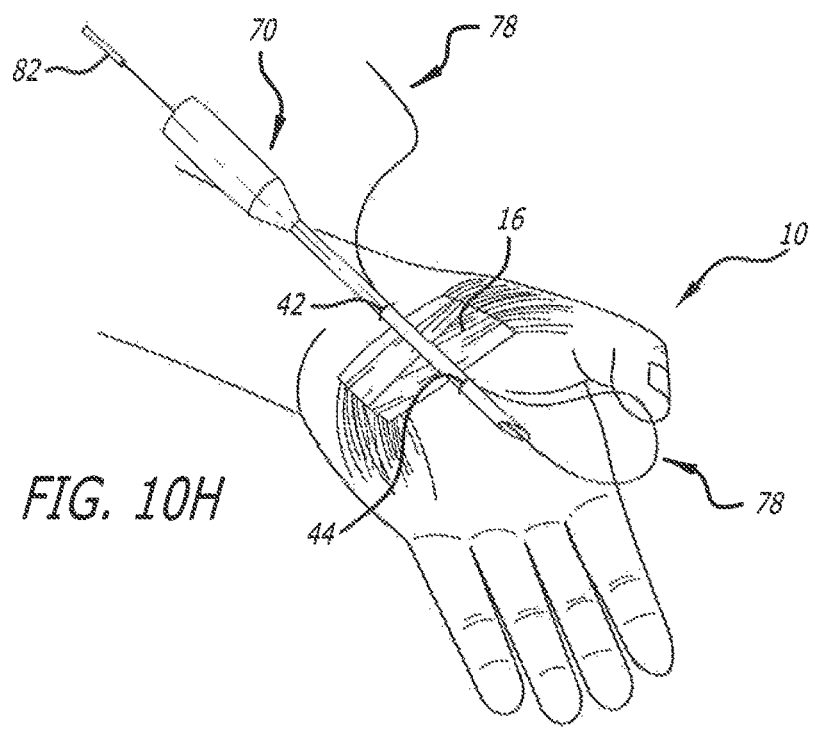
Figure 10I:
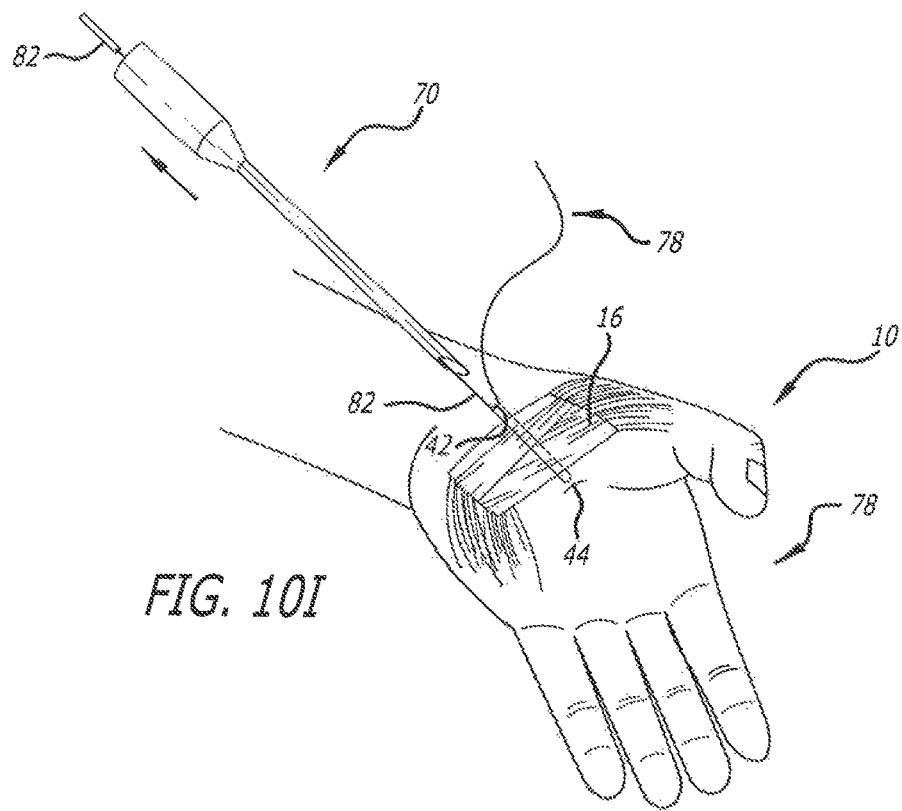
Figure 10J:
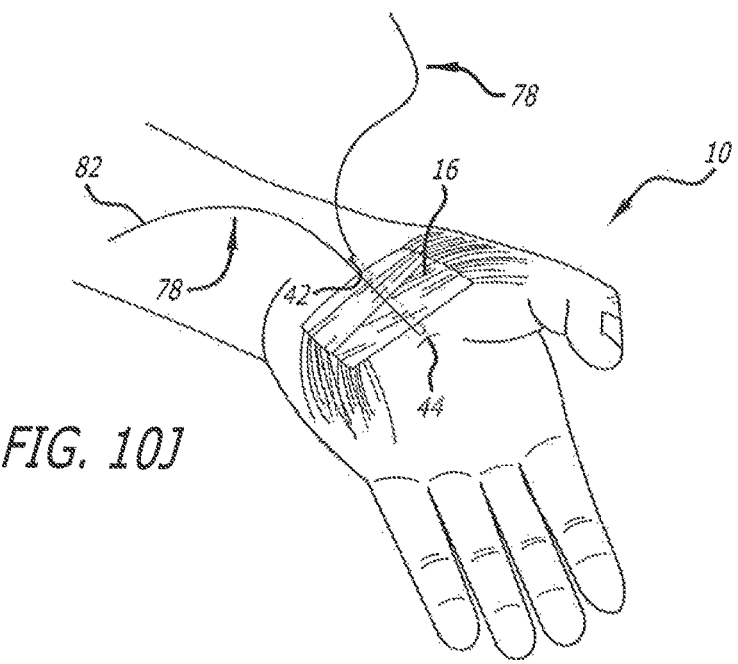

Once the introducer needle 70 is again in place, the cutting element 78 is fed into the distal end of the introducer needle, is extended along the needle's hollow interior to project from its proximal end as is shown in FIG. 10H. Subsequent retraction of the introducer needle as per FIG. 10 I leaves the cutting element in position about the ligament 16 as is shown in FIG. 10J. The cutting element is thereby in position for subsequent manipulation to effect the transection of the ligament.

Alternatively, a cutting element having a stiffened section at both ends allows the cutting element to be initially introduced into the distal end of the introducer needle and extended there through. After retraction of the needle and reintroduction into the hand and extension above the ligament to re-emerge from the hand, the second stiffened end of the cutting element can be inserted into the distal end of the needle and extended there through. Subsequent retraction of the needle again leaves the cutting element in position for the transection.

The cutting element may simply be grasped by the user, may be wound around the hands or fingers of the user for a firmer grip or alternatively, may be fitted with handles to provide for maximum grip and control. Unequal forces can alternatingly be applied to the two ends of the cutting element to induce a reciprocating cutting action either by hand or with the use of an appropriately configured power tool. Alternatively, one end can be pulled with greater force than the other element so as to pull the cutting element in a single direction as it cuts through the ligament. As a further alternative, both ends can be pulled simultaneously with equal force to simply pull the cutting element through the ligament. When transection has been achieved, the cutting element is simply withdrawn through access port 42. Application of a small bandage over each of the access ports 42, 44 completes the procedure.

The goal in implementing the methods disclosed in FIGS. 10A-J and described above in great detail is for the physician to utilize a single introducer needle 70 which enters the patient at a first location (access port 42), traverse one side of the target ligament, and then exit the patient at a second location (access port 44). This method creates a passageway through which the cutting element can be positioned relative to the target ligament for transection purposes. However, due to the sometimes complex anatomy of the patient, this is not always possible. For example, it is sometimes difficult to manipulate the introducer needle or router to exit the patient at the second location due to the presence of thick and stiff tissue mass that may make it almost impossible to target the second location in the patient. As a result of such hard tissue, the physician cannot properly position the distal tip of the introducer needle/router to exit at the second location. Accordingly, there is a need for the physician to reach the second location with the needle/router without causing the distal tip to damage thick tissue located near the second location. The methods disclosed below and depicted in FIGS. 13A-15C provide alternative methods for creating the passageway needed to properly place placing the cutting element when a hard tissue mass is encountered after the introducer needle 70 fails, or is unable to properly exit the second location.

FIGS. 13A-D illustrate other preferred methods of placing a cutting element transverse to the target ligament along a first (bottom) side of the ligament using a pair of hollow introducer needles as the routing tools. These particular methods depict a procedure in which carpal ligament release is being performed. It should be appreciated that the method could also be utilized in any number of different locations in the patient for transecting a soft target body parts, such as tissue and ligaments.

After the area of the hand near and about the transverse carpal ligament 16 has been anesthetized, the distal end 72 of a first hollow introducer needle 70 is brought into contact with the hand just proximal to the proximal edge of the target ligament 16. The ligament 16 is visible in the figures for purposes of clarity only as no incision is made throughout the entire procedure to in any way expose the ligament to view. Additionally, an imaging device, such as an ultrasound device, such as is commonly used for a variety of imaging applications, is used to visualize the position of the introducer needles relative to the ligament but is not shown so as not to obscure the surgical site again for purposes of clarity. It is preferable to enter the hand at a position about 30 mm proximal of the proximal edge of the transverse carpal ligament as the carpal tunnel can then be entered at a shallower angle obviating the need to adjust the angle of the needle after the tunnel has been reached and thereby minimizing trauma to tissue in addition to allowing the introducer needles to be more easily imaged.

In FIG. 13A, the first introducer needle 70 has been advanced into the hand at a first location 42, through the carpal tunnel just under the ligament 16 allowing the distal end 72 to be positioned near a second location 44. At this point, the first introducer needle 70 cannot be advanced any further due to the presence of a hard tissue (not shown) which prevents the distal tip 72 from cleanly exiting the second location 44. The physician then needs to create a way to complete the passageway needed for placing the cutting element in proper position next to the target ligament 16. FIG. 13 B shows a second introducer needle 71 nor being inserted at the second location 44 with its distal end 73 being inserted into the lumen 75 of the first introducer needle 70. As can be seen in FIG. 13B, the diameter of the shaft of the second introducer needle 71 is much smaller than the first introducer needle 70 which allows the second introducer needle 71 to be fully insertable into the lumen 75 of the first needle 70. As can be seen in FIG. 13A, the distal end 72 of the first needle 70 substantially traverses the first side 77 (bottom side) of the ligament 16 and initially remains within the patient until the second introducer needle 71 is inserted into the patient's hand. The distal end 73 of the second needle 71 is inserted into the lumen 75 utilizing an imaging device to visualize the position of the distal ends 72, 73 of the first and second needles 70, 71 in order for the physician to insert the distal end 73 into the lumen 75.

FIG. 13C shows the cutting element 78 extending through the passage formed by the lumens of the first and second introducer needles 70, 71. Subsequently, after the cutting element 78 has been extended through the lumens of the introducer needles 70, 71, the introducer needles 70, 71 can then be retracted from the patient leaving only the cutting element 78 in place adjacent to the first (bottom) side 77 of the ligament 16. As such, a section of cutting element 78 will be left projecting from the first location 42 and the second location 44 while its central section extends through the carpal tunnel just below (adjacent to) one side 77 of the transverse carpal ligament 16.

FIG. 13D shows an alternative method for placing the cutting element into the patient. As can be seen in FIG. 13D, the distal end 72 of the first introducer needle 70 extends out of the second location 44 and outside of the patient's hand. In this regard, the steps depicted in FIGS. 13A and 13B and described above can be initially implemented. The first introducer needle 70 would require a shaft 81 having sufficient length to allows the entire shaft to traverse the ligament 16 and exit out of the second location 44. Instead of leaving the second introducer needle 71 in the patient, the physician advances the first introducer needle over the shaft 79 of the second introducer needle 71, through the opening at the second location 44, allowing the distal end 72 to extend out of the patient, as is shown in FIG. 13D. The cutting element 78 can then be advanced into the lumen of the first introducer needle 70 leaving a section of cutting element 78 projecting from the first location 42 and the second location 44 while its central section extends through the carpal tunnel just below (adjacent to) one side 77 of the transverse carpal ligament 16. The first introducer needle 70 can then be removed from the patient leaving the cutting element 78 in place.

After the cutting element 78 has been placed along the first side 77 of the ligament 16, the method further includes the placement of the cutting element 78 on the other side (top side) of the ligament 16 in order to achieve the cutting method as is shown in FIG. 10J. Preferably, the introducer needle 70 can be placed on the second side 83 of the target ligament utilizing the steps depicted in FIGS. 10F-10J. This method is again preferred since only a single introducer needle 70 is needed to enter the patent at one location, traverse the second side of the ligament, and exit the patient at the second location. However, if hard tissue is again encountered after first attempting to advance the singe introducer needle 70 along the second side of the ligament, then the same method of placing two introducer needles across the side of the ligament, as depicted in FIGS. 13A-D and described above could be implemented for routing the cutting wire 78 to the second (top) side 83 of the ligament 16. In such a method, the lumens of the first and second introducer needles 70, 71 are again interconnected together to form a single passage through which the cutting element can extend. Initially, the first introducer needle 70 is advanced as far as it can be advanced along the second side 83 of the ligament 16. The second introducer needle 71 is then inserted into the second location 44 allowing the needles to interconnect in the region above (the second side) the ligament. Once in place, one end of the cutting element (which has been placed across the first side of the ligament) can be inserted and advanced into the composite passage formed by the lumens of the needles 70, 71 which allows the end to now extend out of the same location as the other end of the cutting element. The two introducer needles 70, 71 can then be removed from the patient leaving the two ends of the cutting element extending from one of the locations 42, 44. Alternatively, the first introducer needle 70 can be advanced over the second introducer needle 71, as is depicted in FIG. 13D, to traverse the second side 83 of the ligament 16. The end of the cutting element could then be advanced through the lumen of the first introducer needle causing both ends of the cutting wire to extend outside the patient at one of the locations 42, 44. The first introducer needle 70 can then be removed from the patient.

Both of these techniques causes the cutting element to be looped around the ligament, i.e., the cutting element 78 will extend around the first and second sides 77, 83 of the ligament 16. The physician can then retract the ends of the cutting element 78 allowing the formed loop of the cutting element to come into contact with the ligament 16 for transection purposes. The cutting element 78 is thereby positioned (looped) around the ligament 16 so that the cutting element 78 remains in position for subsequent manipulation to effect the transection of the ligament.

Figure 14A:
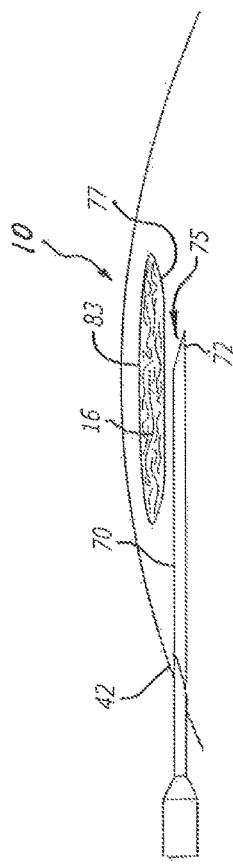
FIGS. 14A-C are cross-sectional views of the hand with a revealed transverse carpal ligament illustrating an alternative preferred sequence of practicing a method of the present invention of placing a cutting element transverse to the target ligament along a first (bottom) side using hollow introducer needles as the routing tool component.
Figure 14B:
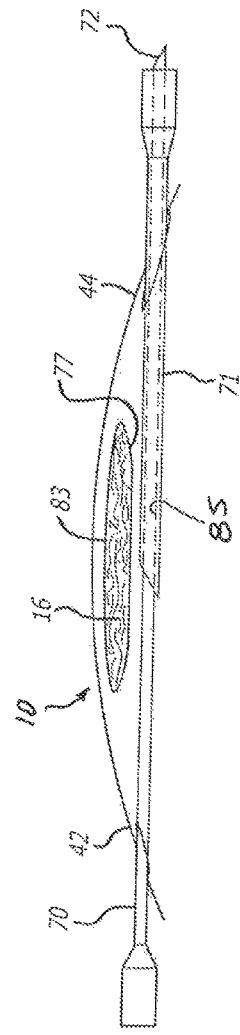
Figure 14C:
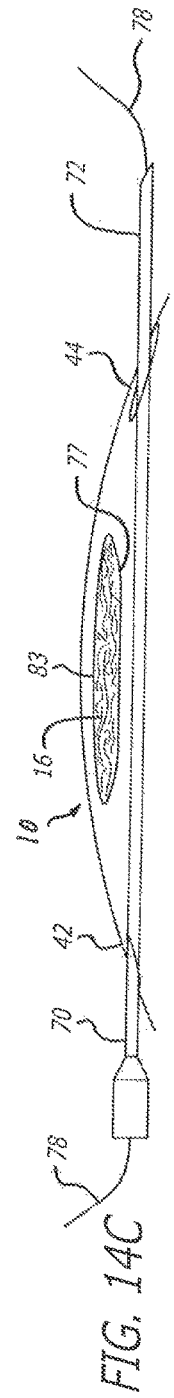

FIGS. 14A-C illustrate another preferred method of placing a cutting element 78 transverse to the target ligament along the first side of the ligament using the same hollow introducer needles depicted in FIGS. 13A-D. In FIG. 14A, the first introducer needle 70 is shown advanced into the hand at the first location 44, through the carpal tunnel just under the ligament 16 allowing its distal end 72 to be positioned adjacent to the first side 77 of the ligament 16. Again, at this point, the first introducer needle 70 cannot be advanced any further due to the presence of a hard tissue which prevents the distal tip 72 from cleanly exiting the second location 44. The physician thus inserts a second introducer needle 71 through the skin at the second location 42. As can be seen in FIG. 14A, the diameter of the needle of the first introducer needle 70 is smaller than the second introducer needle 71 which allows the first introducer needle 70 to be insertable into the lumen of the second introducer needle 71. As can be seen in FIG. 14B, the distal end 72 of the first needle 70 substantially traverses the first side 77 of the ligament 16 as well and remains within the patient. The first introducer needle 70 is then inserted into the lumen of the second introducer needle 71, as is shown in FIG. 14B. The first introducer needle is advanced within the lumen 85 of the second introducer needle 71 inserted until its distal end 72 extends outside of the patient at the second location 44. This technique is similar to the one depicted in FIGS. 13A, 13B and 13D, except the first introducer needle 70 is now advanced within the lumen of the second introducer needle 71 rather than over the shaft 79 of the needle 71. Again, an imaging device, such as an ultrasound device, can be used to visualize the position of the distal ends 72, 73 of the first and second needles 70, 71 in order for the physician to insert the distal end 73 into the lumen 75.

The second introducer needle 71 can then be removed leaving only the distal end 72 of the first introducer needle 70 extending out of the patent, as is shown in FIG. 14B. The cutting element 78 can then be advanced into the lumen of the first introducer needle 70 leaving a section of cutting element 78 projecting from the first location 42 and the second location 44 while its central section extends through the carpal tunnel just below (adjacent to) one side 77 of the transverse carpal ligament 16. The first introducer needle 70 can then be removed from the patient leaving the cutting element 78 in place.

Again, as with the previously described method above, after the cutting element 78 has been placed along the first side 77 of the ligament 16, the method can further include the placement (routing) of the cutting element 78 on the second side (top side) of the ligament 16 in order to achieve the cutting method as is shown in FIG. 10J. Again, the method for routing the cutting element 78 about the second side of the ligament is preferably the steps depicted in FIGS. 10F-10J. However, similar techniques for placing the cutting element on the second side of the ligament can utilize the techniques described above and depicted in FIGS. 14A-C.

These techniques need not be repeated again. Alternatively, the techniques depicted in FIGS. 13A-D could be used to rout the cutting element 78 to the second side of the ligament.

Figure 15A:
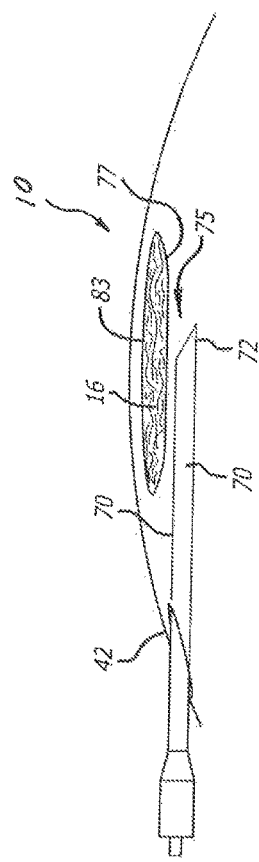
FIGS. 15A-C are cross-sectional views of the hand with a revealed transverse carpal ligament illustrating still another preferred sequence of practicing a method of the present invention of placing a cutting element transverse to the target ligament along a first (bottom) side using hollow introducer needles as the routing tool component.
Figure 15B:
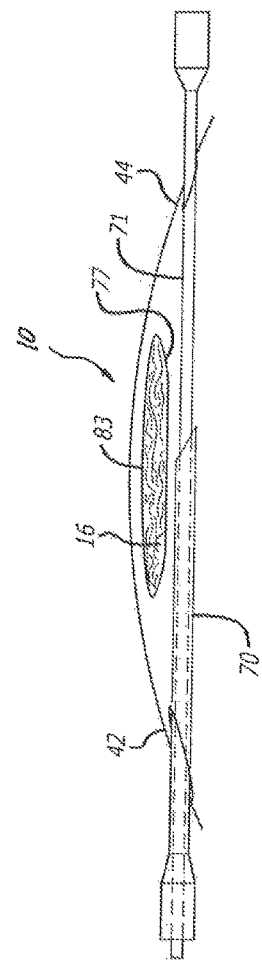
Figure 15C:
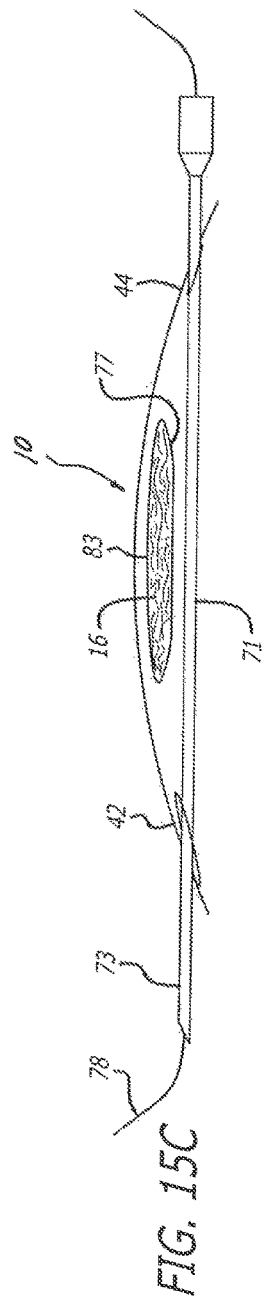

FIGS. 15A-C illustrate yet another preferred method of placing a cutting element transverse to the target ligament along a first (bottom) side of the ligament using a hollow introducer needle as the routing tool. In FIG. 15A, the first introducer needle 70 has been advanced into the hand at the first location 42, through the carpal tunnel just under the ligament 16 allowing the distal end 72 to be positioned near the second location 44 where it can no longer be advanced by the physician. The second introducer needle 71 is then inserted into the patient at the second location 44. As can be seen in FIG. 15B, the diameter of the needle of the first introducer needle 70 is much larger than the second introducer needle 71 which allows the second introducer needle 71 to be insertable into the lumen 75 of the first introducer needle 70 and advanced therein. As can be seen in FIG. 15A, the distal end 72 of the first needle 70 substantially traverses the first side 77 of the ligament 16 and remains within the patient. The second introducer needle 71 is inserted into the patent allowing the distal end 71 of the second introducer needle 71 to be inserted into the lumen 75 of the first introducer needle 70. This second introducer needle 71 can be used to create a portion of the passage that will be formed adjacent the first side 77 of the ligament 16 once the needles are withdrawn from the patient. Again, an imaging device is used to visualize the position of the distal ends 72, 77 of the first and second needles 70, 71.

After the distal end 73 has been inserted into the lumen 75 of the first introducer needle 70, the second introducer needle is advanced within through the lumen 75 and out of the first location 42 where it will remain outside of the patient. The first introducer needle 70 can then be removed leaving only the distal end 73 of the second introducer needle 71 extending out of the patent, as is shown in FIG. 15C.

FIG. 15C further shows the cutting element 78 extending through the lumen 79 of the second introducer needle 71. Subsequently, after the cutting element has be extended through the lumen, the second introducer needle 71 can be retracted leaving only the cutting element 78 in place adjacent the first (bottom) side 77 of the ligament 16. As such, a section of cutting element 78 will be left projecting from both the first access port 42 and the second access port 44 while its central section extends through the carpal tunnel just below or adjacent to one side 77 of the transverse carpal ligament 16.

Again, as with the previously described method above, after the cutting element 78 has been placed along the first side 77 of the ligament 16, the method can further include the placement (routing) of the cutting element 78 on the second side (top side) of the ligament 16 in order to achieve the cutting method as is shown in FIG. 10J. Again, the techniques for placing (routing) the cutting element on the second side of the ligament is preferably the steps depicted in FIGS. 10F-10J. The techniques described above and depicted in FIGS. 15A-C, FIGS. 14A-C, and FIGS. 13A-D could be used if hard tissue is encountered while advancing the first introducer needle 70 across the second side of the ligament.

It should be appreciated that the physician could interchangeably use any of the alternative methods for advancing the introducer needles 70,71 as described above and depicted in FIGS. 13A-15C for routing the cutting element around the ligament. For example, the technique depicted in FIGS. 13A-C and described could be initially used to access the first side of the ligament and the techniques depicted in FIGS. 14A-C or FIGS. 15A-C and described above could be used to access the second side of the ligament.

Figure 11:
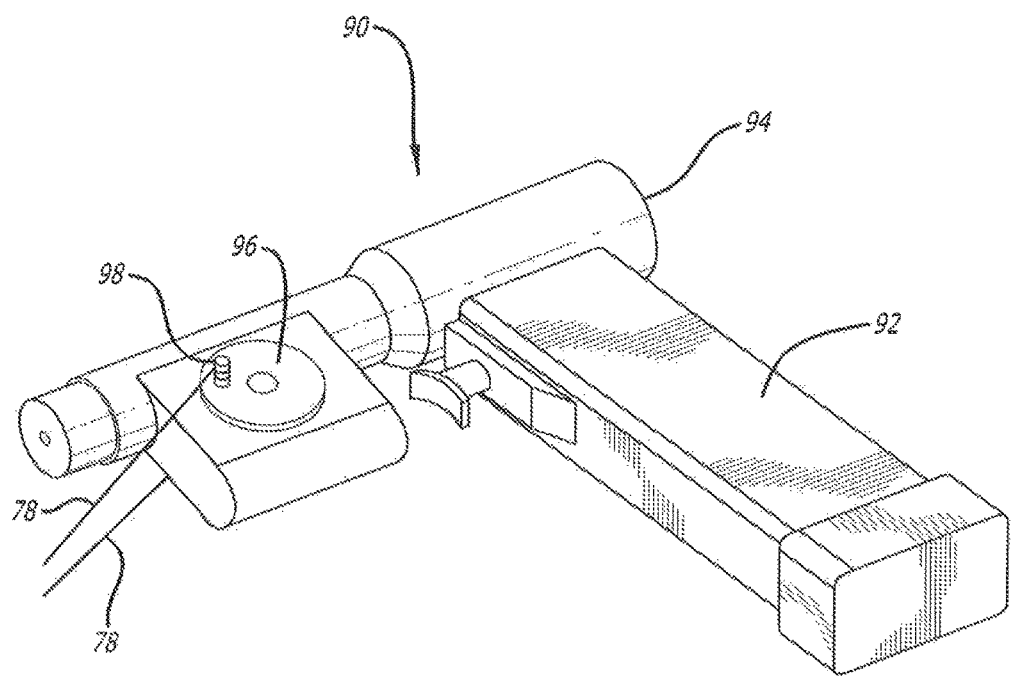
FIG. 11 is a perspective view of a power tool for reciprocating the cutting element once in position about the target ligament.

FIG. 11 generally illustrates a power tool 90 for reciprocating the ends of the cutting element 78. The power tool may include a hand grip section 92, which may house a battery pack. An electric motor would be housed in section 94, rotation of which is mechanically converted to a reciprocating effect. In the embodiment shown, reciprocation is achieved by the rotation of a crankshaft wherein a pin 98 extends from a rotatable disc on each side of the device wherein the pins are diametrically opposed relative one another and to which the ends of the cutting element 78 are attached. Converting the rotation of a longitudinally positioned electric motor to a transversely disposed crankshaft can be achieved in any of various well known ways including for example geared, cammed or desmodromic mechanisms among many others.

Figure 12:
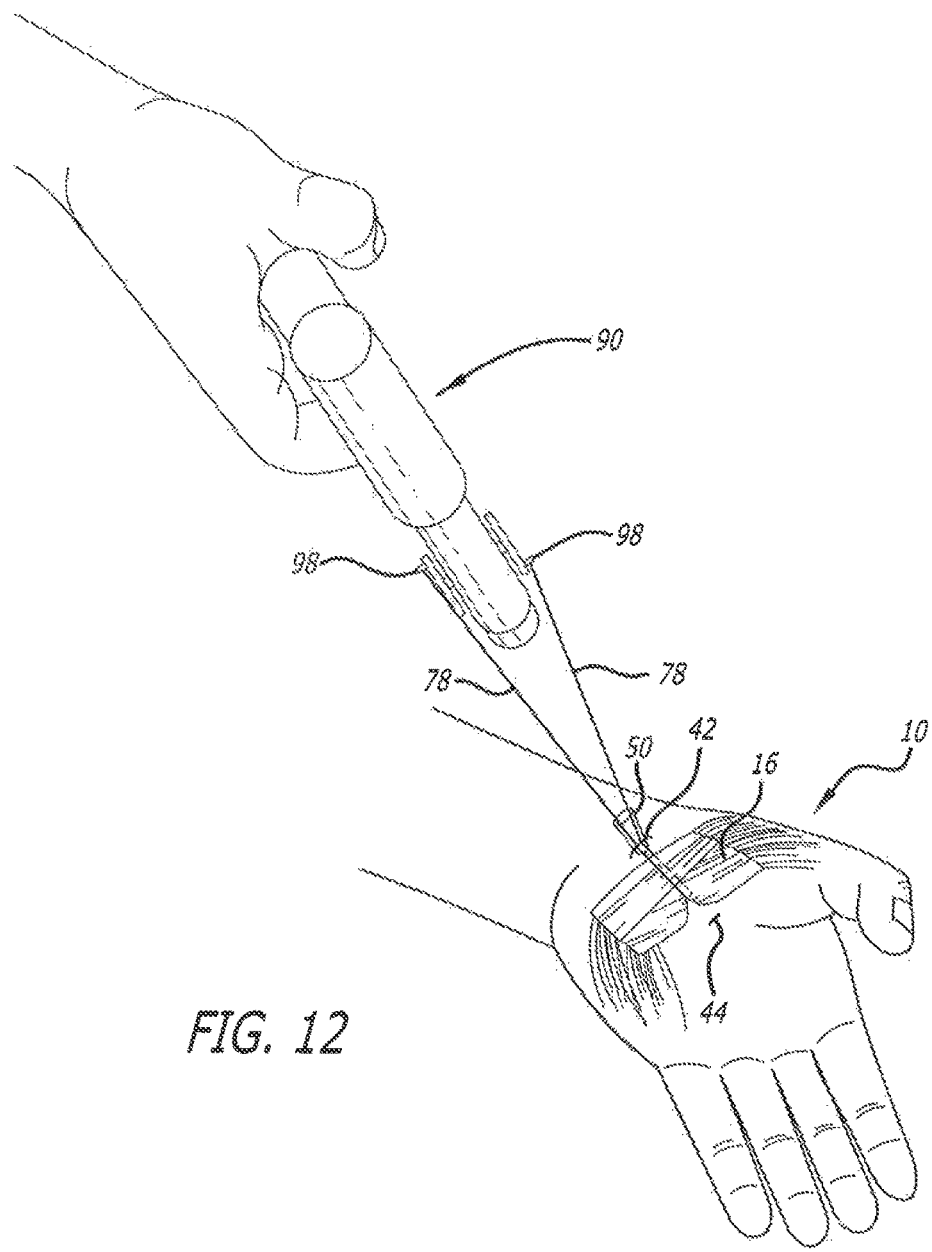
FIG. 12 illustrates the power tool being used to reciprocate the cutting element in place about the ligament.

FIG. 12 illustrates the power tool 90 being used to reciprocate the cutting element 78 in place about the transverse carpal ligament. A protective sleeve 50 may be fitted so as to maintain the two ends of the cutting element in alignment with one another and minimize trauma to the surrounding tissue.

While particular forms of the invention have been described and illustrated, it will also be apparent to those skilled in the art that various modifications can be made without departing from the spirit and scope of the invention. For example, the sequence of steps may be altered so as to cause the retrieval tool to traverse and then retrieve a loop of the cutting element across the top surface of the transverse carpal ligament before traversal of the bottom surface is achieved. Additional access ports may be formed for easier looping of the cutting element. Any of various ports can be used as the final exiting port of the two ends of the cutting element. Additionally, the method and appropriately dimensioned retrieval tool can be used to transect other tissue so as to perform for example, but no limited to, trigger finger release surgery, tarsal tunnel release surgery, plantar fascia release surgery, achilles tendon lengthening surgery, compartment release surgery, cubital tunnel release surgery, fasciotomy surgery, gastrocnemius recession surgery, iliotitial band surgery and pronater release surgery. The apparatus and method can readily be adapted to transect other soft tissue such as for example muscle, tendon, vessels and nerves in humans as well as animals. Accordingly, it is not intended that the invention be limited except by the appended claims.

What is claimed is:

1. A method for transecting a soft tissue within a body, comprising the steps of:
   providing a flexible thread-like cutting element having a smooth and non-abrasive surface;
   providing a first and a second hollow introducer needle, each having a lumen extending therethrough, one of said needles having an internal diameter sufficient to receive said cutting element and having an external diameter capable to be inserted into the lumen of the other needle;
   extending the first hollow introducer needle into the body at a first location transversely adjacent said soft tissue and keeping the first introducer needle inside of the body on a first side of the soft tissue and near a second location transversely adjacent to the soft tissue and opposite the first location;

extending the second introducer needle into the body at the second location and engaging the second introducer needle with the first introducer needle inside the body by inserting the introducer needle into the lumen of the other introducer needle;

extending the cutting element through the lumens of the first and second hollow introducer needles to leave a first end portion of the cutting element projecting proximally and a second end portion projecting distally from the first and second locations respectively;

retracting the first introducer needle from the body so as to leave the cutting element in place;

retracting the second introducer needle from the body so as to leave the cutting element in place;

routing the cutting element transversely adjacent to the soft tissue so as to traverse the soft tissue on a second side thereof opposite the first side;

looping the cutting element about the soft tissue with the first and the second end portions of the cutting element extending out of the body at either the first location or second location; and exerting force on the first and the second end portions of the cutting element so as to achieve a kerf-less transection of the soft tissue.

2. The method of claim 1, wherein said first and second introducer needles are injection needles.

3. The method of claim 1, wherein the steps of routing the cutting element transversely adjacent to the soft tissue so as to traverse the soft tissue on a second side thereof opposite the first side and looping the cutting element about the soft tissue with both end portions of the cutting element extending from the same location of the body, comprising:

re-extending the first introducer needle into the body at the first location transversely adjacent the soft tissue keeping the first introducer needle inside of the body on the second side of the soft tissue and near the second location transversely adjacent to the soft tissue;

re-extending the second introducer needle into the body near the second location and engaging the second introducer needle with the first introducer needle inside the body by inserting one introducer needle into the lumen of the other introducer needle;

guiding the first introducer needle out of the body at the second location by advancing the first introducer needle along the second introducer needle;

retracting the second introducer needle from the body;

inserting the second end portion of the cutting element at the second location into a distal end of the first introducer needle and extending the first end portion through the lumen of the first introducer needle such that the first end portion projects from the first hollow introducer needle; and retracting the first introducer needle from the body so as to leave the cutting element in place.

4. The method of claim 1, wherein the steps of routing the cutting element transversely adjacent to the soft tissue so as to traverse the soft tissue on a second side thereof opposite the first side and looping the cutting element about the soft tissue with both end portions of the cutting element extending from the same location of the body, comprising:

re-extending the first introducer needle into the body at the first location transversely adjacent the soft tissue keeping the first introducer needle inside of the body on the second side of the soft tissue and near the second location transversely adjacent to the soft tissue and opposite the first location;

re-extending the second introducer needle into the body near the second location and engaging the second introducer needle with the first introducer needle inside the body by inserting the introducer needle into the lumen of the other introducer needle;

guiding the second introducer needle out of the body at the first location by advancing the second introducer needle along the first introducer needle;

retracting the first introducer needle from the body;

inserting the first end portion of the cutting element at the first location into a distal end of the second introducer needle and extending the second end portion through the lumen of the second introducer needle such that the second end portion projects from the second hollow introducer needle; and retracting the second introducer needle from the body so as to leave the cutting element in place.

5. A method for transecting a soft tissue within a body, comprising the steps of:

providing a flexible thread-like cutting element having a smooth and non-abrasive surface;

providing a first and a second hollow introducer needle, each having a lumen extending therethrough, one of said needles having an internal diameter sufficient to receive said cutting element and an external diameter capable to be inserted into the lumen of the other needle;

extending the first hollow introducer needle into the body at a first location transversely adjacent said soft tissue and keeping the first introducer needle inside of the body on a first side of the soft tissue and near a second location transversely adjacent to the soft tissue and opposite the first location;

extending the second introducer needle into the body at the second location and engaging the second introducer needle with the first introducer needle inside the body by inserting the introducer needle into the lumen of the other introducer needle;

advancing the first introducer needle along the second introducer needle so that a distal end of the first introducer needle extends out of the body at the second location;

retracting the second introducer needle from the body;

extending a cutting element through the first introducer needle to leave the cutting element projecting proximally and distally from the first and second locations;

retracting the first introducer needle from the body so as to leave the cutting element in place;

routing the cutting element transversely adjacent to the soft tissue so as to traverse the soft tissue on a second side thereof opposite the first side;

looping the cutting element about the soft tissue with a first end portion and a second end portion of the cutting element extending from the same location of the body; and exerting force on the first and second end portions of the cutting element so as to achieve a kerf-less transection of the soft tissue.

6. The method of claim 5, wherein said first and second introducer needles are injection needles.

7. The method of claim 5, wherein the steps of routing the cutting element transversely adjacent to the soft tissue so as to traverse the soft tissue on a second side thereof opposite the first side and looping the cutting element about the soft tissue with both end portions of the cutting element extending from the same location of the body, comprising:

re-extending the first introducer needle into the body at the first location transversely adjacent the soft tissue keeping the first introducer needle inside of the body on the second side of the soft tissue and near the second location transversely adjacent to the soft tissue and opposite the first location;

re-extending the second introducer needle into the body near the second location and engaging the second introducer needle with the first introducer needle inside the body by inserting the introducer needle into the lumen of the other introducer needle;

guiding the first introducer needle out of the body at the second location by advancing the first introducer needle along the second introducer needle;

retracting the second introducer needle from the body;

inserting the first end portion of the cutting element at the second location into the distal end of the first introducer needle and extending the second end portion through the lumen of the first introducer needle such that the second end portion projects from the first hollow introducer needle; and retracting the first introducer needle from the body so as to leave the cutting element in place.

8. The method of claim 5, wherein the steps of routing the cutting element transversely adjacent to the soft tissue so as to traverse the soft tissue on a second side thereof opposite the first side and looping the cutting element about the soft tissue with both end portions of the cutting element extending from the same location of the body, comprising:

re-extending the first introducer needle into the body at the first location transversely adjacent the soft tissue keeping the first introducer needle inside of the body on the second side of the soft tissue and near the second location and transversely adjacent to the soft tissue and opposite the first location;

re-extending the second introducer needle into the body near the second location and engaging the second introducer needle with the first introducer needle inside the body by inserting the introducer needle into the lumen of the other introducer needle;

guiding the second introducer needle out of the body at the first location by advancing the second introducer needle along the first introducer needle;

retracting the first introducer needle from the body;

inserting the first end portion of the cutting element at the first location into a distal end of the second introducer needle and extending the second end portion through the lumen of the second introducer needle such that the second end portion projects from the second hollow introducer needle; and retracting the second introducer needle from the body so as to leave the cutting element in place.

9. A method for transecting a soft tissue within a body, comprising the steps of:

providing a flexible thread-like cutting element having a smooth and non-abrasive surface;

providing a first and a second hollow introducer needle, each having a lumen extending therethrough, one of said needles having an internal diameter sufficient to receive said cutting element and having an external diameter capable to be inserted into the lumen of the other needle;

extending the first hollow introducer needle into the body at a first location transversely adjacent said soft tissue and keeping the first introducer needle inside of the body on a first side of the soft tissue and near a second location transversely adjacent to the soft tissue and opposite the first location;

extending the second introducer needle into the body at the second location and engaging the second introducer needle with the first introducer needle inside the body by inserting the introducer needle into the lumen of the other introducer needle;

advancing the second introducer needle along the first introducer needle so that a distal end of the second introducer needle extends out of the body at the first location;

retracting the first introducer needle from the body;

extending the cutting element through the second introducer needle to leave the cutting element projecting proximally and distally from the first and second locations;

retracting the second introducer needle from the body so as to leave the cutting element in place;

routing the cutting element transversely adjacent to the soft tissue so as to traverse the soft tissue on a second side thereof opposite the first side;

looping the cutting element about the soft tissue with a first end portion and a second end portion of the cutting element extending from the same location of the body; and exerting force on the first and second end portions of the cutting element so as to achieve a kerf-less transection of the soft tissue.

10. The method of claim 9, wherein said first and second introducer needles are injection needles.

11. The method of claim 9, wherein the steps of routing the cutting element transversely adjacent to the soft tissue so as to traverse the soft tissue on a second side thereof opposite the first side and looping the cutting element about the soft tissue with both end portions of the cutting element extending from the same location of the body comprising:

re-extending the first introducer needle into the body at the first location transversely adjacent the soft tissue keeping the first introducer needle inside of the body on the second side of the soft tissue and near the second location transversely adjacent to the soft tissue and opposite the first location;

re-extending the second introducer needle into the body near the second location and engaging the second introducer needle with the first introducer needle inside the body by inserting one introducer needle into the lumen of the other introducer needle;

guiding the first introducer needle out of the body at the second location by advancing the first introducer needle along the second introducer needle;

retracting the second introducer needle from the body;

inserting the first end portion of the cutting element at the second location into a distal end of the first introducer needle and extending the second end portion through the lumen of the first introducer needle such that the second end portion projects from the first hollow introducer needle; and retracting the first introducer needle from the body so as to leave the cutting element in place.

12. The method of claim 9, wherein the steps of routing the cutting element transversely adjacent to the soft tissue so as to traverse the soft tissue on a second side thereof opposite the first side and looping the cutting element about the soft tissue with both end portions of the cutting element extending from the same location of the body comprising:

re-extending the first introducer needle into the body at the first location transversely adjacent the soft tissue keeping the first introducer needle inside of the body on the second side of the soft tissue and near the second location transversely adjacent to the soft tissue and opposite the first location;

re-extending the second introducer needle into the body near the second location and engaging the second introducer needle with the first introducer needle inside the body by inserting the introducer needle into the lumen of the other introducer needle;

guiding the second introducer needle out of the body at the first location by advancing the second introducer needle along the first introducer needle;

retracting the first introducer needle from the body;

inserting the first end portion of the cutting element at the first location into the distal end of the second introducer needle and extending the second end portion through the lumen of the second introducer needle such that the second end portion projects from the second hollow introducer needle; and retracting the second introducer needle from the body so as to leave the cutting element in place.

* * * * *